United States Patent [19]
Chow et al.

[11] Patent Number: 5,965,410
[45] Date of Patent: Oct. 12, 1999

[54] ELECTRICAL CURRENT FOR CONTROLLING FLUID PARAMETERS IN MICROCHANNELS

[75] Inventors: Calvin Y. H. Chow; Anne R. Kopf-Sill, both of Portola Valley; J. Wallace Parce, Palo Alto, all of Calif.

[73] Assignee: Caliper Technologies Corp., Mountain View, Calif.

[21] Appl. No.: 08/977,528

[22] Filed: Nov. 25, 1997

Related U.S. Application Data

[60] Provisional application No. 60/056,058, Sep. 2, 1997.

[51] Int. Cl.$^6$ ..................................................... C12P 19/34
[52] U.S. Cl. ........................... 435/91.2; 435/6; 435/91.1; 204/450
[58] Field of Search ............................ 435/6, 91.1, 91.2; 204/450, 451, 454, 600, 604, 609, 612

[56] References Cited

U.S. PATENT DOCUMENTS

| | | |
|---|---|---|
| 3,987,362 | 10/1976 | McCann et al. ........................... 324/30 |
| 4,675,300 | 6/1987 | Zare et al. . |
| 4,683,195 | 7/1987 | Mullis et al. . |
| 4,683,202 | 7/1987 | Mullis et al. . |
| 4,800,159 | 1/1989 | Mullis et al. . |
| 4,908,112 | 3/1990 | Pace . |
| 4,963,498 | 10/1990 | Hillman et al. . |
| 4,965,188 | 10/1990 | Mullis et al. . |
| 5,126,022 | 6/1992 | Soane et al. . |
| 5,176,203 | 1/1993 | Larzul . |
| 5,194,133 | 3/1993 | Clark et al. . |
| 5,207,886 | 5/1993 | Lauer et al. . |
| 5,270,183 | 12/1993 | Corbett et al. . |
| 5,281,516 | 1/1994 | Stapleton et al. . |
| 5,333,675 | 8/1994 | Mullis et al. . |
| 5,346,672 | 9/1994 | Stapleton et al. . |
| 5,498,392 | 3/1996 | Wilding et al. . |
| 5,527,670 | 6/1996 | Stanley . |
| 5,529,752 | 6/1996 | Pontis et al. . |
| 5,571,410 | 11/1996 | Swedberg et al. . |
| 5,585,069 | 12/1996 | Zanzucchi et al. . |
| 5,587,128 | 12/1996 | Wilding et al. . |

(List continued on next page.)

FOREIGN PATENT DOCUMENTS

| | | | |
|---|---|---|---|
| WO 96/04547 | 2/1996 | WIPO | ............................ G01N 27/00 |
| WO 97/02357 | 1/1997 | WIPO | ............................ C12P 19/34 |

OTHER PUBLICATIONS

Moeller et al Chemistry with Inorganic Qualitative Analysis p. 565, 1980.

Dasgupta, P.K. et al., "Electroosmosis: A Reliable Fluid Propulsion System for Flow Injection Analysis," *Anal. Chem.* 66:1792–1798 (1994).

Manz, A. et al., "Electroosmotic pumping and electrophoretic separations for miniaturized chemical analysis systems," *J. Micromech. Microeng.* 4:257–265 (1994).

Ramsey, J.M. et al., "Microfabricated chemical measurement systems," *Nature Medicine* 1 (10):1093–1096 (1995).

Seiler, K. et al., "Electroosomotic Pumping and Valveless Control of Fluid Flow within a Manifold of Capillaries on a Glass Chip," *Anal. Chem.* 66 (20):3485–3491 (1994).

*Primary Examiner*—Kenneth R. Horlick
*Assistant Examiner*—Jeffrey Siew
*Attorney, Agent, or Firm*—Matthew B. Murphy

[57] ABSTRACT

A novel method and device for transporting and/or monitoring a fluid in a multi-port device 400, 800, 1000 used in a microfluidic system is provided. The multi-port device includes a substrate having a novel channel configuration. A first channel region 413 having a first port and a second port for transporting fluid therebetween is defined in the substrate. A second channel region 421 having a first port and a second port for applying electric current for heating fluid or for monitoring a fluid parameter therebetween is also defined in the substrate. In some embodiments, the first channel intersects 407 with the second channel. The heating or monitoring aspect of the invention can be used with a variety of biological reactions such as PCR, LCR, and others.

38 Claims, 13 Drawing Sheets

U.S. PATENT DOCUMENTS

| | | |
|---|---|---|
| 5,589,136 | 12/1996 | Northrup et al. . |
| 5,603,351 | 2/1997 | Cherukuri et al. . |
| 5,607,832 | 3/1997 | Stanley et al. . |
| 5,637,469 | 6/1997 | Wilding et al. ......................... 435/7.21 |
| 5,639,423 | 6/1997 | Northrup et al. . |
| 5,641,400 | 6/1997 | Kaltenbach et al. . |
| 5,646,039 | 7/1997 | Northrup et al. . |
| 5,674,742 | 10/1997 | Northrup et al. . |
| 5,699,157 | 12/1997 | Parce . |
| 5,779,868 | 7/1998 | Parce et al. ............................ 204/604 |
| 5,800,690 | 9/1998 | Chow et al. ............................ 204/451 |
| 5,810,985 | 9/1998 | Bao et al. . |

ELECTRICAL CURRENT FOR CONTROLLING FLUID PARAMETERS IN MICROCHANNELS

This application claims the benefit of U.S. Provisional Application No. 60/056,058, filed Sep. 2, 1997, which is incorporated herein by reference in its entirety for all purposes.

BACKGROUND OF THE INVENTION

The present invention generally relates to microfluidic systems. More particularly, the present invention provides a technique, including methods and devices, for providing and controlling heat to fluid in a channel of a microfluidic system in an efficient manner. Merely by way of example, the invention is applied to a polymerase chain reaction process, commonly termed PCR, but it will be recognized that the invention has a much wider range of applicability. The invention also provides techniques for monitoring and controlling a variety of process parameters using resistivity and/or conductivity measurements.

There has been a growing interest in the manufacture and use of microfluidic systems for the acquisition of chemical and biochemical information. Techniques commonly associated with the semiconductor electronics industry, such as photolithography, wet chemical etching, etc., are being used in the fabrication of these microfluidic systems. The term, "microfluidic", refers to a system or device or "chip" having channels and chambers which are generally fabricated at the micron or submicron scale, e.g., having at least one cross-sectional dimension in the range of from about 0.1 $\mu$m to about 500 $\mu$m. Early discussions of the use of planar chip technology for the fabrication of microfluidic systems are provided in Manz et al., *Trends in Anal. Chem.* (1990) 10(5):144–149 and Manz et al., *Adv. in Chromatog.* (1993) 33:1–66, which describe the fabrication of such fluidic devices and particularly microcapillary devices, in silicon and glass substrates.

Applications of microfluidic systems are myriad. For example, International Patent Appln. WO 96/04547, published Feb. 15, 1996, describes the use of microfluidic systems for capillary electrophoresis, liquid chromatography, flow injection analysis, and chemical reaction and synthesis. U.S. Appln. No. 08/671,987, entitled "HIGH THROUGHPUT SCREENING ASSAY SYSTEMS IN MICROSCALE FLUIDIC DEVICES", filed on Jun. 28, 1996 by J. Wallace Parce et al., and assigned to the present assignee, discloses wide ranging applications microfluidic systems in rapidly assaying large number of compounds for their effects on chemical, and preferably, biochemical systems. The phrase, "biochemical system", generally refers to a chemical interaction which involves molecules of the type generally found within living organisms. Such interactions include the full range of catabolic and anabolic reactions which occur in living systems including enzymatic, binding, signaling and other reactions. Biochemical systems of particular interest include, e.g., receptor-ligand interactions, enzyme-substrate interactions, cellular signaling pathways, transport reactions involving model barrier systems (e.g., cells or membrane fractions) for bio-availability screening, and a variety of other general systems.

Many chemical or biological systems also desire control over processing parameters such as temperature, concentration of reagents, buffers, salts and other materials, and the like. In particular, some chemical or biological systems require processes to be carried out at controlled or varied temperature. In providing such a controlled temperature in miniaturized fluidic systems, external heating elements have generally been used. Such heating elements typically include external resistive heating coils or material, which provide heat to the fluidic system in a conductive manner. This heating unit attaches itself directly to an external portion of the chip to globally heat the chip and to provide a uniform temperature distribution to be present on the chip. This heating unit, however, is cumbersome. It also complicates chip manufacturing and often affects quality and reliability of the chip. Additionally, the resistive heating element often fails, which can damage the chip, equipment, and the environment. Furthermore, the resistive heating element generally cannot effectively control heat supplied to the chip, which often causes large undesirable temperature gradients and fluctuations in the chip. Accordingly, the resistive heating element applied directly to the chip is extremely limited (e.g., cannot heat locally) and unreliable in controlling process temperature in the chip.

Larger scale temperature controllers have also been used to control reaction temperatures within a reaction vessel, including, e.g., hot-plates, water baths, and the like. These larger temperature control elements have been commonly employed in biological and chemical laboratory environments to heat fluid in beakers, test tubes, and the like. Unfortunately, such controllers are not well suited to providing accurate control of temperature within a microfluidic system. In fact, such global heating systems heat the entire material region of the microfluidic device and cannot be used to selectively apply heat to specific regions of the microfluidic device, e.g., specific channels or chambers. Additionally, these large temperature controllers, e.g., hot plates, often require large resistive heating elements, which transfer heat via conduction. These resistive heating elements possess a large characteristic response time, which often relates to a long time to heat or cool material within a reaction vessel in contact therewith in some applications. Accordingly, hot plates can be extremely limited for use in heating fluid in microfluidic applications.

Other process parameters in the microfluidic system such as fluid concentration, pH, and the like typically cannot be controlled by way of conventional techniques. A user of the microfluidic system often verifies fluid concentration or pH at the fluid source (e.g., bottle), but the user generally cannot monitor such fluid parameters while the fluid in being used in the microfluidic system using conventional techniques. In fact, there is simply no easy or efficient way to check these parameters once the fluid enters into channels or processing chambers of the microfluidic system. Accordingly, it is often difficult, if not impossible, to verify the integrity of a process by monitoring these process parameters.

From the above, it is seen that a technique for selectively controlling a variety of process parameters in a microfluidic system that is easy, efficient, and safe is highly desirable.

SUMMARY OF THE INVENTION

According to the present invention, techniques including methods and devices for controlling process parameters such as fluid temperature, concentration and the like of material (e.g., fluid) in a microfluidic system is provided. The present invention uses, for example, electric current applied through the material for heating purposes. Since only a small volume of the material is heated, the material can be successively heated and cooled by controlling the application of electric current to the material for a variety of chemical and biological applications, e.g., PCR and others. Additionally, the invention provides techniques for monitoring process parameters such as temperature, fluid concentration, pH, and the like during a process step. Accordingly, an in-situ technique for monitoring these process parameters is provided.

In one aspect, the present invention provides a microfluidic system having a controlled temperature element. In particular, the system comprises a substrate having at least a first fluid-filled microscale channel disposed therein. The system also includes a means for elevating a temperature of the fluid in the first portion of the channel, by applying a first controlled electrical current or voltage through the first portion of the channel. The current is optionally applied through the first channel or through a second channel intersecting the first channel. Regions may be selectively heated by providing those regions with different, e.g., narrower cross-sectional areas, to increase the current density in those regions, and thus, the heat generated from that current.

In a related aspect, the present invention provides a microfluidic system having one or more thermal elements included therein. The system comprises a first channel defined in a substrate, where the channel includes a first end and a second end. A first energy source is provided coupled between the first end and the second end of the channel. The first energy source is further set at a current or voltage such that a fluid is pumped through said first channel. A second energy source is also provided coupled to the fluid in the first channel, whereby a voltage from the energy source such that a portion of said fluid is heated in a portion of said first capillary channel.

In still another related aspect, the present invention provides a microfluidic system, that comprises a capillary channel comprising a first end and a second end, and an energy source coupled between the first end and the second end. The energy source provides a voltage across the fluid such that a portion of a fluid is heated in a portion of the capillary channel.

In a further related aspect, the present invention provides a microfluidic system, which comprises a capillary channel defined in a substrate, the channel comprising fluid therein, wherein the capillary channel has a region whereupon fluid in the region is selectively heated using a voltage bias applied to the fluid in the capillary channel.

In still a further related aspect, the present invention provides a microfluidic system, which comprises a substrate, a channel defined in the substrate which channel includes a first end and a second end. An energy source is coupled to the channel, which energy source comprises a first source comprising an AC component and a second source comprising a DC component.

In an alternate, but still related aspect, the present invention provides a microfluidic system having a temperature control device. In particular, the system comprises a substrate and a channel defined in the substrate. The channel comprises a first end and a second end. An energy source is coupled to the channel to provide current through a fluid in said channel the current heating the fluid in the channel. A sensor is additionally coupled to the channel to detect a temperature of the fluid in the channel. A controller coupled to the sensor and the energy source controls the temperature in the channel based upon a desired set-point temperature.

The present invention also provides a multi-port, microfluidic device, which comprises a substrate having a first fluid-filled channel region defined therein. The substrate includes at least a first port and a second port for transporting a material therebetween, and a second channel region defined in the substrate for applying electric current for heating fluid between the first and second ports.

The present invention also provides a computer program product for operating a microfluidic system in accordance with other aspects of the present invention. In particular, the computer program comprises a computer readable memory including a code that directs an energy source to adjust an electric current or voltage to a channel comprising a fluid therein, to heat the fluid to a selected elevated level.

The present invention also provides methods of controlling temperatures in microfluidic systems. In particular, in one aspect, the present invention provides a method of elevating temperature in at least a first portion of a fluid-filled microscale channel disposed in a substrate, to a first selected elevated temperature. The method typically comprises applying a first selectable current through the first portion of the first channel, wherein the first portion of the first channel has a first electrical resistance. At least one of the first selectable current or the first electrical resistance is then controlled to elevate the temperature in the first portion of the first channel to a first selected elevated temperature.

In a related aspect, the present invention provides a method of heating fluid in a microfluidic system, which comprises providing a channel, disposed in a substrate, having a first end, a second end, and a region defined therebetween. A fluid is provided in at least the region of the channel. An electric current is applied through the fluid to heat the fluid in the region. Further, the electric current selectively heats the fluid in the region of the channel while preventing substantial heating of the fluid outside the region. In yet a further related aspect, the present invention provides a method for controlling temperature of fluid in a channel defined in a substrate of a microfluidic system, which method comprises applying an electrical source to begin heating said fluid in said channel, adjusting a first parameter from the electrical source to provide a relatively constant second parameter. Wherein the fluid is heated without substantially increasing a temperature of the substrate.

In another aspect, the present invention provides a method for monitoring parameters of a process in a microfluidic system. The method comprises providing a microfluidic system that includes a channel defined in a substrate. A material is transported in the channel, and the conductivity value of the material in the channel is determined. The conductivity measured in the measuring step is then correlated to a particular process parameter, i.e., buffer concentration, pH or temperature.

In a further aspect, the methods and systems of the present invention are useful in performing aqueous reactions at superheated temperatures. Specifically, such reactions are carried out by placing aqueous reactants into a microscale channel that is disposed in a solid substrate, and which has two ends, each end having an electrical port. The channel has at least a first electrical resistance associated with it whereby application of an electrical current through the channel results in heating of the aqueous reactants to temperatures in excess of 100° C.

DETAILED DESCRIPTION OF THE INVENTION

Figure 1:
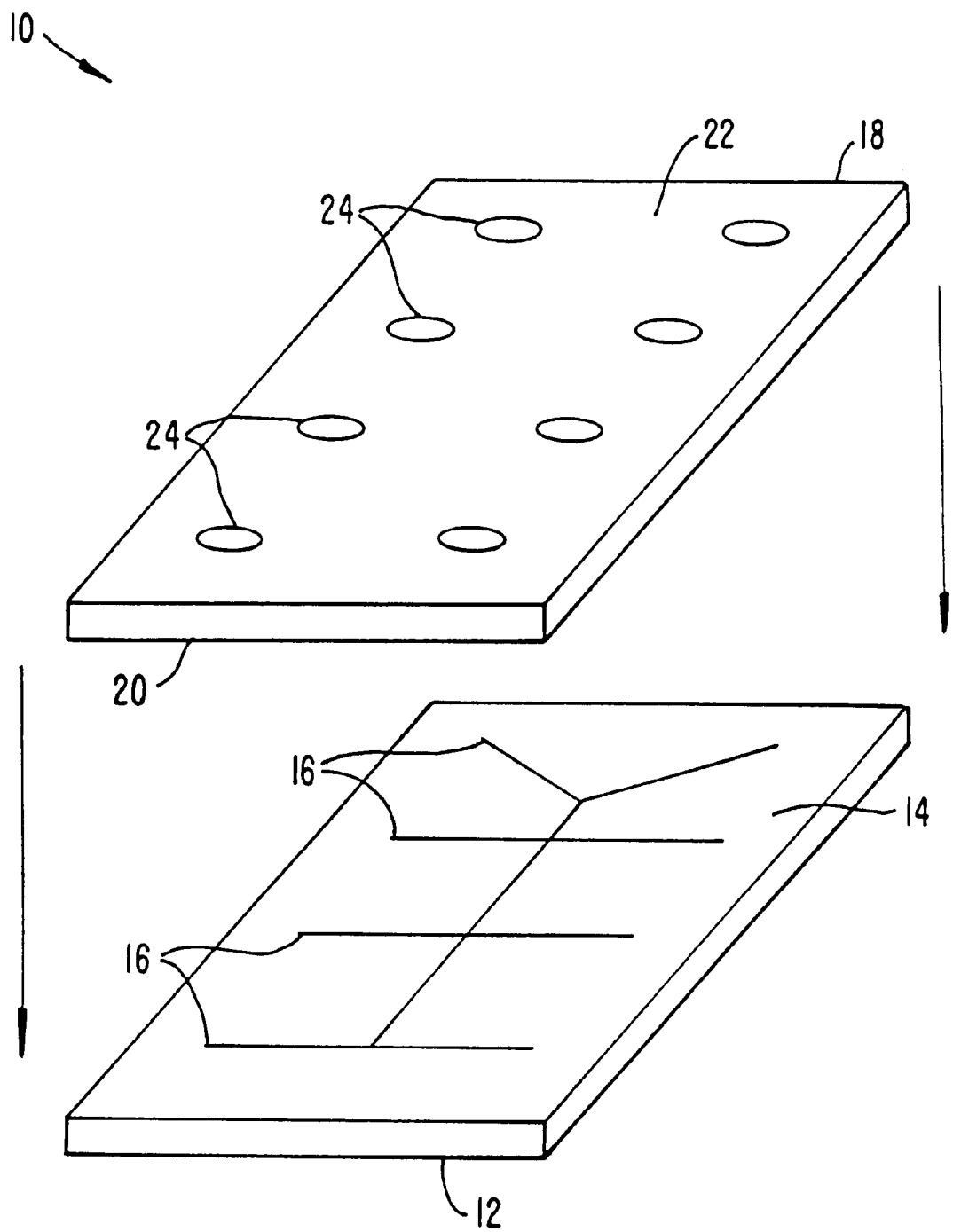
FIG. 1 is a simplified schematic illustration of an embodiment of a microfluidic system.

The present invention provides techniques for heating and cooling fluids in a microfluidic system, as well as monitoring a variety of process parameters. In exemplary embodiments, the present invention also provides techniques for moving and heating fluids through channels or annular regions of a microfluidic system. In particular, the present invention uses energy such as, for example, electric current, as heating source for providing regional or global heating of a fluid in a microfluidic channel. Details of the present invention are provided below in reference to the Figures that were already briefly described. Before discussing the embodiments directed to heating and cooling fluids by way of the novel heating sources and process monitoring embodiments, it may assist the reader to understand the context of the present invention by way of the next section.

I. Microfluidic Systems, Generally

As used herein, the terms "microscale" or "microfabricated" generally refers to structural elements or features of a device which have at least one fabricated dimension in the range of from about 0.1~$\mu$m to about 500~$\mu$m. Thus, a device referred to as being microfabricated or microscale will include at least one structural element or feature having such a dimension. When used to describe a fluidic element, such as a passage, chamber or conduit, the terms "microscale", "microfabricated" or "microfluidic" generally refer to one or more fluid passages, chambers or conduits which have at least one internal cross-sectional dimension, e.g., depth, width, length, diameter, etc., that is less than 500 $\mu$m, and typically between about 0.1 $\mu$m and about 500 $\mu$m. In the devices of the present invention, the microscale channels or chambers preferably have at least one cross-sectional dimension between about 0.1 $\mu$m and 200 $\mu$m, more preferably between about 0.1 $\mu$m and 100 $\mu$m, and often between about 0.1 $\mu$m and 20 $\mu$m. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication. Body structures may be integrated structures, or may be aggregations of multiple separate parts that fit together to form the aggregate body structure.

Typically, the body structure of the microfluidic devices described herein comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device.

FIG. 1 illustrates a two-layer body structure 10, for a microfluidic device. In preferred aspects, the bottom portion of the device 12 comprises a solid substrate that is substantially planar in structure, and which has at least one substantially flat upper surface 14. A variety of substrate materials may be employed as the bottom portion. Typically, because the devices are microfabricated, substrate materials will be selected based upon their compatibility with known microfabrication techniques, e.g., photolithography, wet chemical etching, laser ablation, air abrasion techniques, injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents. Although preferred substrates are planar in structure, it will be appreciated that a variety of substrate conformations may be utilized, including concave or convex structures, tubular structures, e.g., capillaries, and the like.

In additional preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. patent application Ser. No. 08/843,212, filed Apr. 14, 1997, U.S. Pat. No. 5,885,470, and which is incorporated herein by reference in its entirety for all purposes. Further, such alternate substrates may be in any of a variety of conformations, e.g., planar, tubular, concave, convex, or the like.

The channels and/or chambers of the microfluidic devices are typically fabricated into the upper surface of the bottom substrate or portion 12, as microscale grooves or indentations 16, using the above described microfabrication techniques. The top portion or substrate 18 also comprises a first planar surface 20, and a second surface 22 opposite the first planar surface 20. In the microfluidic devices prepared in accordance with the methods described herein, the top portion also includes a plurality of apertures, holes or ports 24 disposed therethrough, e.g., from the first planar surface 20 to the second surface 22 opposite the first planar surface.

The first planar surface 20 of the top substrate 18 is then mated, e.g., placed into contact with, and bonded to the planar surface 14 of the bottom substrate 12, covering and sealing the grooves and/or indentations 16 in the surface of the bottom substrate, to form the channels and/or chambers (i.e., the interior portion) of the device at the interface of these two components. The holes 24 in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

In many embodiments, the microfluidic devices will include an optical detection window disposed across one or more channels and/or chambers of the device. Optical detection windows are typically transparent such that they are capable of transmitting an optical signal from the channel/chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

These devices may be used in a variety of applications, including, e.g., the performance of high throughput screening assays in drug discovery, immunoassays, diagnostics, genetic analysis, and the like. As such, the devices described herein, will often include multiple sample introduction ports or reservoirs, for the parallel or serial introduction and analysis of multiple samples. Alternatively, these devices may be coupled to a sample introduction port, e.g., a pipettor, which serially introduces multiple samples into the device for analysis. Examples of such sample introduction systems are described in e.g., U.S. patent application Ser. Nos. 08/761,575 and 08/760,446 each of which was filed on Dec. 6, 1996, and is hereby incorporated by reference in its entirety for all purposes.

In preferred aspects, the devices, methods and systems described herein, employ electrokinetic material transport systems, and preferably, controlled electrokinetic material transport systems. As used herein, "electrokinetic material transport systems" include systems which transport and direct materials within an interconnected channel and/or chamber containing structure, through the application of electrical fields to the materials, thereby causing material movement through and among the channel and/or chambers.

Although the preferred aspects of the present invention generally employ electrokinetic transport of materials in microfluidic systems, it is easily recognized that the heating and control aspects of the present invention are readily adaptable to systems utilizing other material transport systems. For example, pressure based or pneumatic flow systems using pumps and/or pressure sources external to the microfluidic device can be used in conjunction with the heating, sensing and control aspects of the present invention. Similarly, integrated microfluidic devices, e.g., incorporating microfabricated pump and valve structures, integrated into the device, are also readily adaptable for use with these heating and control systems.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure, which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel will cause the proton sheath to move in the direction of the voltage drop, i.e., toward the negative electrode, pulling the bulk fluid along with it.

"Controlled electrokinetic material transport and direction", as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves, which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner.

Although described for the purposes of illustration with respect to a four way, cross intersection, these controlled electrokinetic material transport systems can be readily adapted for more complex interconnected channel networks, e.g., arrays of interconnected parallel channels.

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquoting, and the like. Similarly, downstream operations may include similar operations, including, e.g., separation of sample components, labeling of components, assays and detection operations. Assay and detection operations include without limitation, probe interrogation assays, e.g., nucleic acid hybridization assays utilizing individual probes, free or tethered within the channels or chambers of the device and/or probe arrays having large numbers of different, discretely positioned probes, receptor/ligand assays, immunoassays, and the like.

The systems described herein generally include microfluidic devices, as described above, in conjunction with additional instrumentation for controlling fluid transport and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

A variety of controlling instrumentation may be utilized in conjunction with the microfluidic devices described above, for controlling the transport and direction of fluids and/or materials within the devices of the present invention. For example, in many cases, fluid transport and direction may be controlled in whole or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. In such systems, fluid direction is often accomplished through the incorporation of microfabricated valves, which restrict fluid flow in a controllable manner. See, e.g., U.S. Pat. No. 5,171,132.

As noted above, the systems described herein preferably utilize electrokinetic material direction and transport systems. As such, the controller systems for use in conjunction with the microfluidic devices typically include an electrical power supply and circuitry for concurrently delivering appropriate voltages to a plurality of electrodes that are placed in electrical contact with the fluids contained within the microfluidic devices. Examples of particularly preferred electrical controllers include those described in, e.g., U.S. patent application Ser. No. 08/888,064 and International Patent Application No. US97/12930 filed Jul. 2, 1997 (Attorney Docket Nos. 17646-000610U5 and 000610PC, respectively), the disclosures of which are hereby incorporated herein by reference in their entirety for all purposes. In brief, the controller uses electric current control in the microfluidic system. The electrical current flow at a given electrode is directly related to the ionic flow along the channel(s) connecting the reservoir in which the electrode is placed. This is in contrast to the requirement of determining voltages at various nodes along the channel in a voltage control system. Thus the voltages at the electrodes of the microfluidic system are set responsive to the electric currents flowing through the various electrodes of the system. This current control is less susceptible to dimensional variations in the process of creating the microfluidic system in the device itself. Current control permits far easier operations for pumping, valving, dispensing, mixing and concentrating subject materials and buffer fluids in a complex microfluidic system. Current control is also preferred for moderating undesired temperature effects within the channels.

In the microfluidic systems described herein, a variety of detection methods and systems may be employed, depending upon the specific operation that is being performed by the system. Often, a microfluidic system will employ multiple different detection systems for monitoring the output of the system. Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensory communication with the device, channel, or chamber. The phrase "within sensory communication" of a particular region or element, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself.

Particularly preferred detection systems include optical detection systems for detecting an optical property of a material within the channels and/or chambers of the microfluidic devices that are incorporated into the microfluidic systems described herein. Such optical detection systems are typically placed adjacent a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the materials spectral characteristics. In preferred aspects, the detector measures an amount of light emitted from the material, such as a fluorescent or chemiluminescent material.

As such, the detection system will typically include collection optics for gathering a light based signal transmitted through the detection window, and transmitting that signal to an appropriate light detector. Microscope objectives of varying power, field diameter, and focal length may be readily utilized as at least a portion of this optical train. The light detectors may be photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to the computer (described in greater detail below), via an AD/DA converter, for transmitting detected light data to the computer for analysis, storage and data manipulation.

In the case of fluorescent materials, the detector will typically include a light source which produces light at an appropriate wavelength for activating the fluorescent material, as well as optics for directing the light source through the detection window to the material contained in the channel or chamber. The light source may be any number of light sources that provides the appropriate wavelength, including lasers, laser diodes and LEDs. Other light sources may be required for other detection systems. For example, broad band light sources are typically used in light scattering/transmissivity detection schemes, and the like. Typically, light selection parameters are well known to those of skill in the art.

The detector may exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

As noted above, and as described in greater detail below, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an AD/DA converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

II. Temperature Control In Microfluidic Systems

As noted previously, the present invention is generally directed microfluidic systems which selectively provide energy to heat materials, e.g., fluids, including samples, analytes, buffers and reagents, in a desired location(s), e.g., within selected channels and/or chambers, of the microfluidic device in an efficient manner. In particular, the present invention uses a power source(s) that passes electrical current through fluid that is disposed within the channels and/or chambers of microfluidic systems, for heating that material in a controlled manner. The present invention, therefore, takes the art recognized problem of resistive electrical heating of fluids in electrically controlled systems, and utilizes it to the advantage of the experimenter, e.g., to perform heating and control operations, within microfluidic systems.

The methods and systems of the present invention provide a multitude of advantages over typical temperature control methods for fluidic systems. For example, such systems provide an ease of control and automation that come with precise electrical control of the temperature. Further such systems provide advantages of speed in changing temperatures of fluids and materials within channels. Additionally, these systems are readily integrated into state of the art electrokinetic microfluidic systems. Finally, such methods and systems permit the precise regional control of temperature control and/or heating within separate microfluidic elements of a given device, e.g., within one or several separate channels in a given device, without heating other regions where such heating is less desired. In particular, in accordance with the presently described methods and systems, heat is only generated within the fluidic elements where such heating is desired. Further, because such microfluidic elements are extremely small in comparison to the mass of the substrate in which they are fabricated, such heat remains substantially localized, e.g., it dissipates into and from the substrate before it affects other fluidic elements. In other words, the relatively massive substrate functions as a heat sink for the separate fluidic elements contained therein. Thus, in accordance with the present invention, one can selectively heat materials in one or more channels of an integrated microfluidic channel system, e.g., having multiple intersecting channels, or multiple channels that are closely packed together on a single substrate or body structure, while not substantially altering the temperature of material in other channels on the substrate or intersecting with the heated channel. By "not substantially altering the temperature", is meant that the temperature of material in the "non-heated" channel(s) will not vary more than about 40% (in terms of degrees C.) from the temperature of the temperature of the overall substrate, e.g., typically ambient temperature. For example, if the ambient temperature of the substrate prior to any heating is 20° C., then heating of one channel portion within that substrate will occur without elevating the remaining channel portions more than 40%, or 8° C. In preferred aspects, the temperature of the remaining, unheated channel portions will not vary more than 10% and more preferably, not more than about 5%. Of course where a channel intersects a heated channel, a portion of that channel will be subjected to elevated temperatures, e.g., at or near the intersection. However, the majority of the channel portion, e.g., greater than 90% is maintained at or near ambient temperatures. Alternatively, unheated channels are maintained within about 10° C. of the temperature at which they would be absent any eating on the chip, preferably, within about 5° C., and more preferably within about 2° C.

In its simplest embodiment, the present invention provides a microfluidic device having at least a first microscale channel having a fluid material disposed therein. A power source, electrically coupled to different points along the channel, controllably delivers a current through the fluid within the channel to elevate the temperature of that fluid in a controlled, localized manner, i.e., localized within the fluid. A large number of modifications can be made to the basic principles, in order to apply the present invention broadly to a large number of applications, and many of these are described in greater detail below. For example, the heating current may be applied directly to the channel or chamber in which an elevated temperature is desired, to portions of that channel, or it may be applied to an auxiliary, heating channel, e.g., that intersects or is adjacent to the channel in which the material to be heated is disposed.

Because electrical energy is used to control temperature directly within the fluids contained in the microfluidic devices, the invention is preferably utilized in microfluidic systems that employ electrokinetic material transport systems, as noted above. Specifically, the same electrical controllers, power supplies and electrodes can be readily used to control temperature contemporaneously with their control of material transport. This is discussed in greater detail below.

In exemplary embodiments, the material is disposed within and preferably passes through a channel in which temperature control is desired. The channel typically has a desired cross-section (e.g., diameter, width or depth) that enhances the heating effects of the current passed therethrough, and the thermal transfer of energy from the current to the fluid. The channel(s) described herein can be formed on almost any type of substrate material such as, for example, amorphous materials (e.g., glass, plastic, silicon), composites, multi-layered materials, combinations thereof, and the like, as described in greater detail, above.

To assist in the understanding of the present invention, it may be helpful to briefly describe the present embodiments directed to heating fluid as described herein. In general, electric current passing through the fluid in a channel produces heat by dissipating energy through the electrical resistance of the fluid. Power dissipates as the current passes through the fluid and goes into the fluid as energy as a function of time to heat the fluid. The following mathematical expression generally describes a relationship between power, electrical current, and fluid resistance:

where POWER=power dissipated in fluid; I=electric current passing through fluid; and R=electric resistance of fluid.

The above equation provides a relationship between power dissipated ("POWER") to current ("I") and resistance ("R"). In some of the embodiments, which are directed toward moving the fluid, a portion of the power goes into kinetic energy of moving the fluid through the channel. The present embodiment uses a selected portion of the power to heat the fluid in the channel or a selected channel region(s). This channel region is often narrower or smaller in cross-section than other channel regions in the channel structure. The smaller cross-section provides higher resistance in the fluid, which increases the temperature of the fluid as electric current passes therethrough. Alternatively, the electric current can be increased along the length of the channel by increased voltage, which also increases the amount of power dissipated into the fluid to correspondingly increase fluid temperature.

Figure 2:
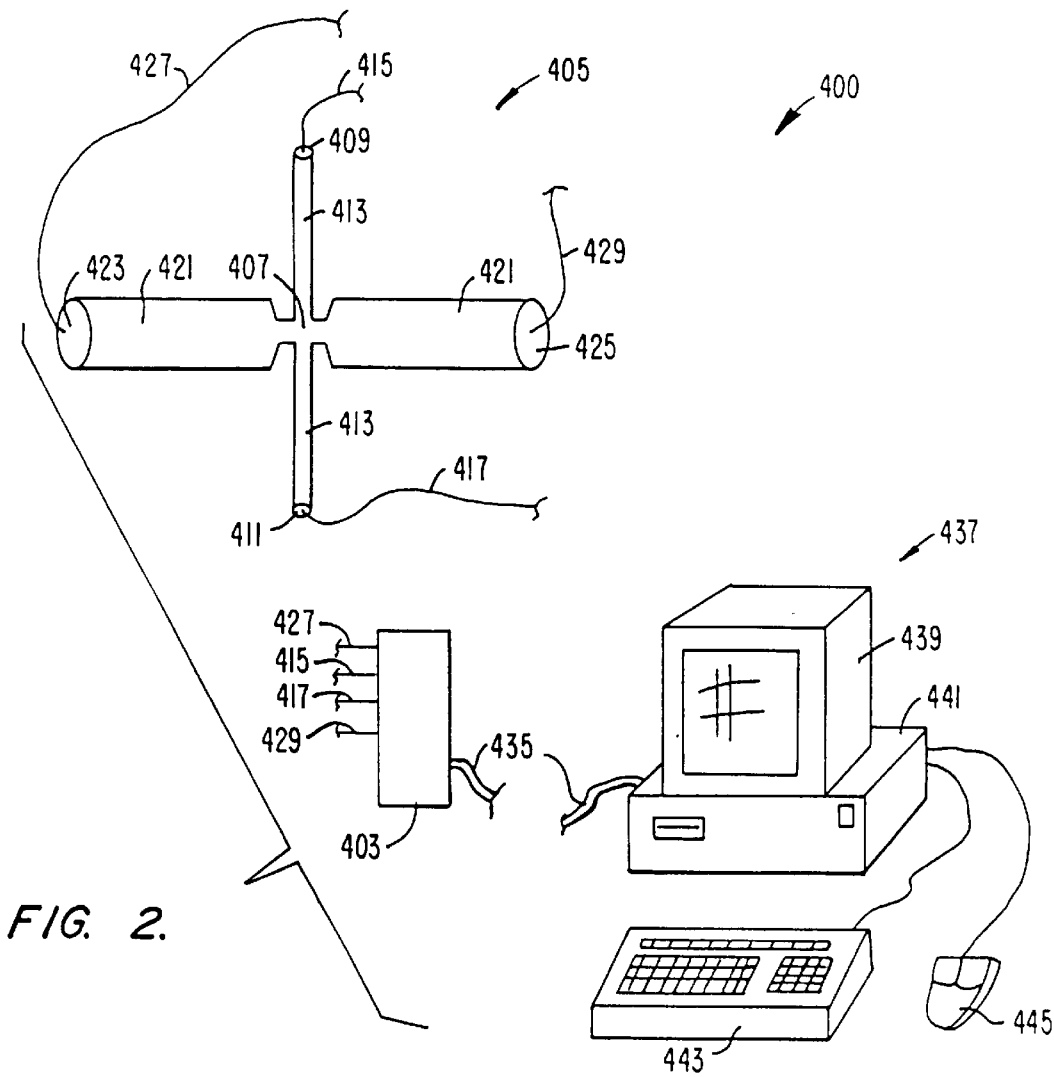
FIG. 2 is a simplified diagram of a microfluidic system with a heating source according to the present invention.

FIG. 2 is a simplified diagram of one example of a microfluidic system 400 with a heating source according to the present invention. The diagram is merely an illustration and should not limit the scope of the claims herein. One of ordinary skill in the art would recognize other variations, alternatives, and modifications. The diagram illustrates a channel network or configuration 405 for moving and heating a volume of material, e.g., fluid, in channel or capillary region 407, which is located at the intersection of channels 413 and 421. Channel 413 can have a similar length and width such as those described herein, but can also be others. Channel 413 connects to regions 409 and 411. Regions 409 and 411 supply power to channel 413 for moving the fluid between regions 409 and 411. Material is moved between these regions by electrokinetic effects, e.g., electroosmotic and/or electrophoretic forces, such as those previously described herein, but is not limited to these effects. Power supply 403 provides power through lines 415 and 417 to regions 409 and 411, respectively. In particular, power supply 403 provides a voltage differential or electric field between regions 409 and 411 by application of a voltage differential to electrodes in regions 409 and 411, which voltage differential drives the electrokinetic movement of the material. As shown, the voltage differential applies along the length of channel 413.

Preferably, power supply 403 also provides power to regions 423 and 425 for the purpose of heating the fluid and material in region 407 in the channel configuration. In particular, power supply 403 provides a voltage differential between regions 423 and 425, resulting in an electric current between regions 423 and 425. The electric current is used to distribute energy to the fluid and material in region 407 for at least heating purposes. Channel 421 includes a novel geometric configuration, which is designed to effectively heat the fluid in region 407 in an efficient manner. As shown, channel 421 includes outer portions 421, each having a larger width or cross-sectional (e.g., diameter) dimension than inner portion or region 407, which has a corresponding larger fluid or electrical resistance than outer portions 421. The precise dimensions of the wider and narrower portions can be optimized depending upon the amount of current applied through the system, the amount of desired heating, the thermal capacity of the substrates and the like, which can be easily optimized experimentally. In any event, such dimensions typically fall within the dimensions described for microscale channels, herein, e.g., at least one cross-sectional dimension between 0.1 and 500 $\mu$m.

To selectively control the temperature of fluid or material at region 407 of the channel, power supply 403 applies voltage and/or current in one of many ways. For instance, power supply 403 applies direct current (i.e., DC), which passes through channel 421 and into channel region 407 which is smaller in cross-section to heat fluid and material in region 407. This direct current can be selectively adjusted in magnitude to complement any voltage or electric field that may be applied between regions 409 and 411 to move materials in and out of region 407. In order to heat the material within region 407, without adversely affecting the movement of that material, alternating current (i.e., AC) can be selectively applied by the power supply 403 through channel 421 and into channel region 407 to heat fluid in region 407. This alternating current used to heat the fluid can be selectively adjusted to complement voltage or electric field that may be applied between regions 409 and 411 to move fluid in and out of region 407. AC current, voltage, and/or frequency can be adjusted, for example, to heat the fluid without substantially moving the fluid. Alternatively, power supply 403 applies a pulse or impulse of current and/or voltage, which passes through channel 421 and into channel region 407 to heat fluid in region 407 at a given instance in time. This pulse can be selectively adjusted to complement any voltage or electric field that may be applied between regions 409 and 411 to move materials, e.g., fluids or other materials, in and out of region 407. Pulse width, shape, and/or intensity can be adjusted, for example, to heat the fluid substantially without moving the fluids or materials, or to heat the material while moving the fluid or materials. Still further, the power supply may apply any combination of DC, AC, and pulse, depending upon the application.

A controller or computer 437 such as a personal computer, commonly termed PC, monitors the temperature of the fluid in region 407 of the channel. The controller or computer receives current and voltage information from, for example, the power supply and identifies or detects temperature of fluid in region 407 in the channel. Depending upon the desired temperature of fluid in region 407, controller or computer adjusts voltage and/or current to meet the desired fluid temperature. The controller or computer also can be set to be "current controlled" or "voltage controlled" or "power controlled" depending upon the application. Controller or computer 437 includes a monitor 439, which is often a cathode ray tube ("CRT") display, a flat panel display (e.g., active matrix liquid crystal display, liquid crystal display), and others. Computer circuitry is often placed in a box 441, which includes numerous integrated circuit chips, such as a microprocessor, memory, interface circuits, and others. The box 441 also includes a hard disk drive, a floppy disk drive, a high capacity drive (e.g., ZipDrive™ sold by Iomega Corporation), and other elements. Also shown are keyboard 443 and mouse 445, which provide for a human interface to computer box 441. A variety of techniques by way of a computer program can be used to detect and monitor temperature, as well as other process parameters. Some of these techniques are described in more detail below.

In some embodiments, computer 437 is coupled to a network such as a local or wide area network. The local network can be configured as, for example, Ethernet or Token Ring. The local area network can also be an "Intranet." Any one or a combination of these local area networks can be connected to a wide area network such as the "Internet" among others. The network can also be wireless, depending upon the application. The network allows for users to be off-site or allows multiple users to monitor or control or view processes of the present microfluidic system.

Figure 2A:
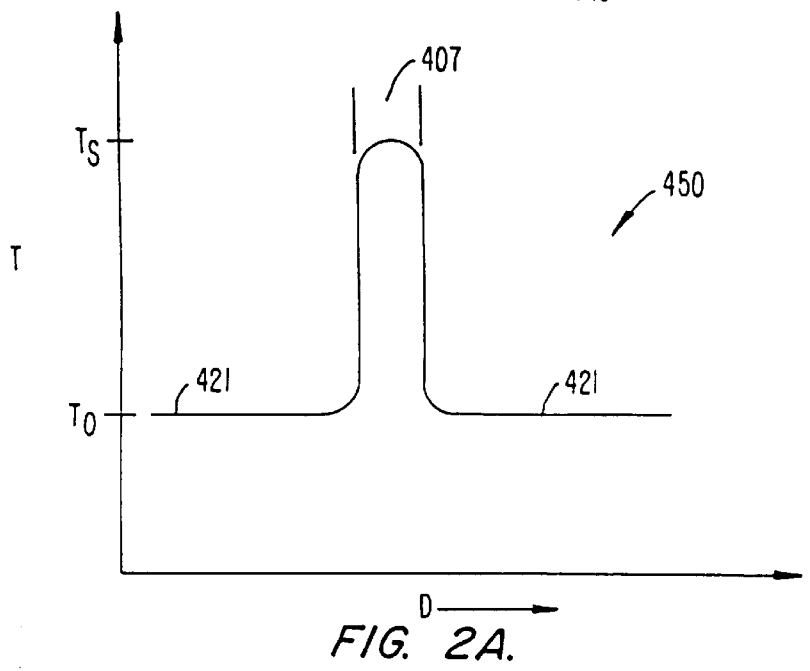
FIG. 2A is a simplified diagram of a temperature profile in the system of FIG. 2.

The embodiment shown in FIG. 2, for example, provides a higher fluid or material temperature in the channel at region 407 than at peripheral regions 421. FIG. 2A is a simplified diagram of temperature distribution 450 along the channel. As shown, the vertical axis represents temperature ("T") and the horizontal axis represents length or distance ("D") along the channel. Fluid in channel region 421 is maintained at temperature $T_o$. Fluid in channel region 407 is maintained at temperature $T_s$. The fluid temperature at region 407 is higher than the fluid temperature at region 421 as a result of the higher current density (and higher resistance) at region 407 from the cross-section of the channel at region 407 being smaller relative to the cross-section of the channel in region 421. Depending upon the shape of the channel, the temperature profile from one end of the channel to the other end of the channel can vary selectively. As can be appreciated, temperature control along the length of the channel can be varied by varying the cross-sectional dimension of that channel, while allowing the current to remain unchanged.

Figure 3:
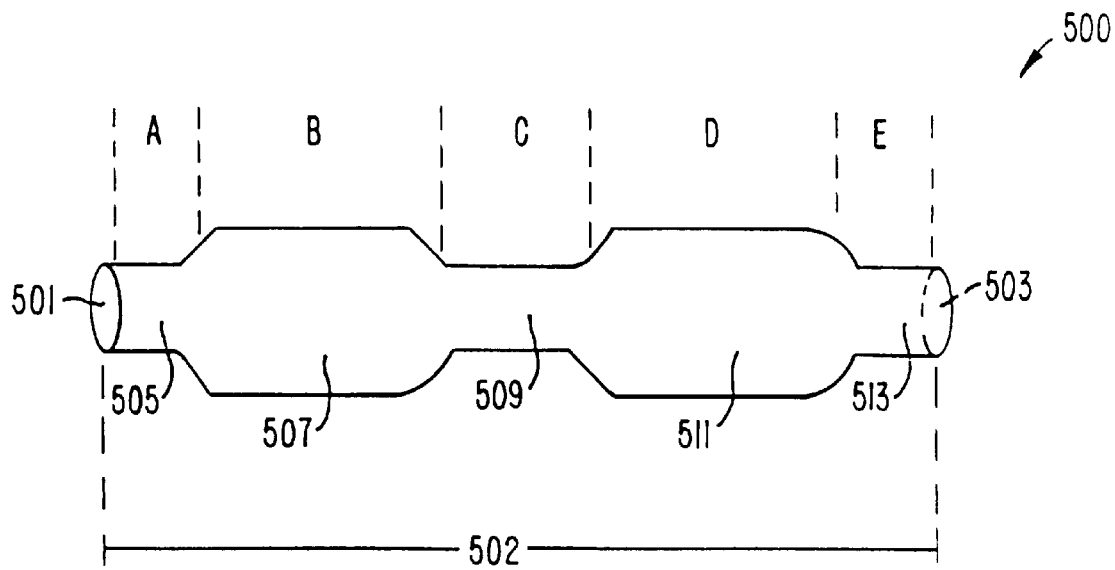
FIG. 3 is a simplified diagram of a microfluidic system with a heating source according to an alternative embodiment of the present invention.

FIG. 3 is a simplified diagram of a microfluidic system 500 with a heating source according to an alternative embodiment of the present invention. This diagram is merely an illustration and should not limit the scope of the claims herein. One of ordinary skill in the art would recognize other variations, alternatives, and modifications. The microfluidic system 500 includes a channel 502 having a variety of temperature zones, e.g., A, B, C, D, E, and fluid therein.

A power supply, such as the one described above, provides electric current between regions 501 and 503 for the purpose of heating fluid in region 505, 509 and 513 of the channel configuration. The power supply also provides a voltage differential between regions 501 and 503 that drives the transport of material through channel 502. The electric current is used, at least in part, to distribute energy to fluid in region 509 for at least heating purposes. The power supply (or another power supply) can also drive or move fluid between regions 501 and 503.

Channel 502 includes a novel geometric configuration, which is designed to heat the fluid in region 505, 509 and 513 in an efficient manner. As shown, channel 502 includes outer portions 507, 511 that each has a larger width or cross-section dimension than inner portion or region 509. Additionally, regions 505 and 513 that attach, respectively, to regions 501 and 503, each has a smaller width or cross-section dimension than outer portions 507 and 511. The narrower dimensions result in an increased current density within these regions when a current is passed through channel 502, resulting in a heating of the fluid located within these regions. Accordingly, fluid also increases in temperature in regions 505 and 513. Material can also be transported from region 501 to 503 while being heated in region 509, allowing heating of only a portion of the material. Further, additional regions of narrower dimension are optionally provided along the length of channel 502, to provide thermal cycling, "on the fly, " as material is transported along channel 502.

In a specific embodiment, fluid is heated in certain regions and cools in other regions. In particular, fluid in regions 507 and 511 is cooler than fluid in regions 505, 509, and 513. Additionally, channel 502 can be coupled to other channels, which move fluid from one region of channel 502 to another region of channel 502. Still further, the power supplied between regions 501 and 503 can be varied depending upon the application. For instance, the power source supplies energy in the form of electric current and/or voltage across regions 501 and 503. The electric current and/or voltage can be DC, AC, pulsed, a combination thereof, and others. Of course, the type of power used depends upon the application.

Figure 4:
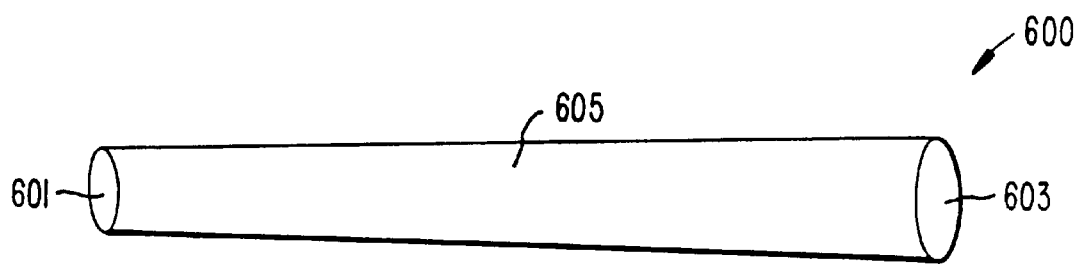
FIG. 4 is a simplified diagram of a microfluidic system with a heating source according to yet another alternative embodiment of the present invention.

FIG. 4 is a simplified diagram of a microfluidic system 600 with a heating source according to yet another embodiment of the present invention. This diagram is merely an illustration and should not limit the scope of the claims herein. One of ordinary skill in the art would recognize other variations, alternatives, and modifications. This diagram illustrates a channel 605, which gradually increases in cross-section from region 601 to region 603. A power source provides a voltage differential between regions 601 and 603. The voltage differential causes or drives a current to flow through fluid between regions 601 and 603. Current density near region 601 is higher than current density near region 603, which provides fluid at a higher temperature near region 601. The power supplied between regions 601 and 603 can be varied depending upon the application. For instance, the power source supplies energy in the form of electric current and/or voltage across regions 601 and 603. The electric current and/or voltage can be direct, alternating, pulsed, a combination thereof, and others. Of course, the type of power used depends upon the application.

Material can also be electrokinetically moved or transported from region 601 to 603 while the fluid is being cooled from region 601 to 603. Moving fluid and/or material increases in temperature from region 603 to region 601 by way of the present embodiment. Alternatively, moving the material from region 601 to 603 decreases its temperature or cools it as it is being transported or moved from region 603 to region 601. Material movement or flow occurs using any of the techniques described herein and others. Of course, the particular combination of fluid movement and heating or cooling depends upon the application.

Figure 5:
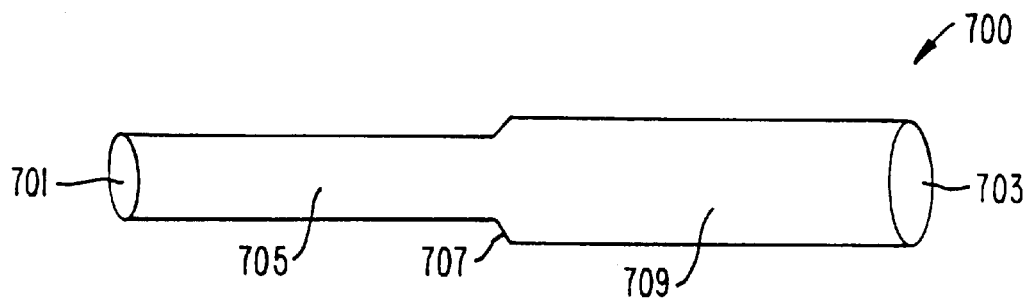
FIG. 5 is a simplified diagram of a microfluidic system with a heating source according to still another alternative embodiment of the present invention.

FIG. 5 is a simplified diagram of a microfluidic system 700 with a heating source according to yet another embodiment of the present invention. This diagram is merely an illustration and should not limit the scope of the claims herein. One of ordinary skill in the art would recognize other variations, alternatives, and modifications. This microfluidic system 700 includes a channel having region 705 with a first cross-section and region 709 with a second cross-section, wherein the second cross-section is larger than the first cross-section. Transition region 707 is located between regions 705 and 709.

Power is supplied between regions 701 and 703. In particular, power is applied to fluid in channel 705 and 709 using electrodes applied to the fluid. Since the cross-section of channel 705 is smaller than the cross-section of channel 709, the temperature of fluid in channel 705 is greater than the temperature of fluid in channel 709. A power source supplies energy in the form of electric current and/or voltage across regions 701 and 703. The electric current and/or voltage can be direct, alternating, pulsed, a combination thereof, and others. Of course, the type of power used depends upon the application.

In combination with cooling the fluid, fluid and/or material also is moved from region 705 to region 709. Fluid is moved or is transported between region 705 to region 709 using any of the techniques described herein and others. During this transport, the fluid or material cools. Alternatively, fluid or material is moved from region 709 to region 705 in combination with heating the fluid at region 707. Of course, the particular combination of fluid movement and heating or cooling depends upon the application.

Figure 6:
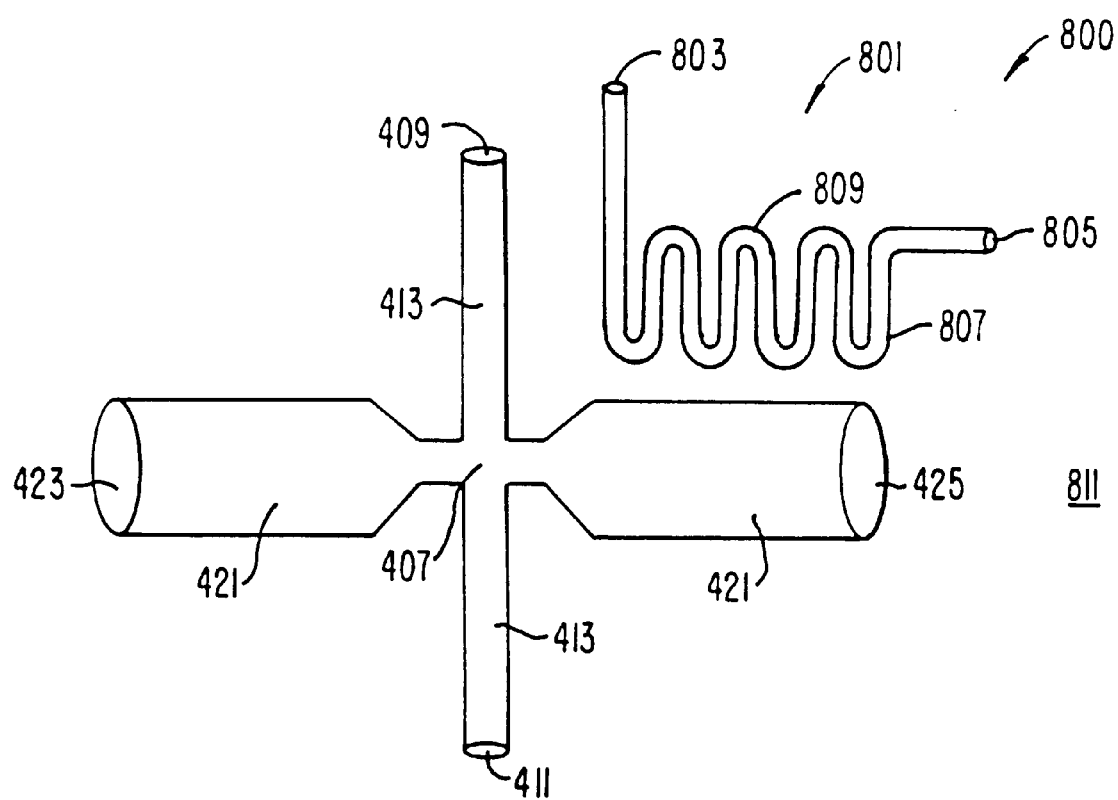
FIG. 6 is a simplified diagram of a microfluidic system with a heating source according to still a further alternative embodiment of the present invention.

In an alternative embodiment, FIG. 6 is a simplified diagram of another example of a microfluidic system 800 according to the present invention. This diagram is merely an illustration and should not limit the scope of the claims herein. One of ordinary skill in the art would recognize other variations, alternatives, and modifications. As shown in FIG. 6, the alternate embodiment of the present invention is illustrated in conjunction with a channel structure or network as shown in FIG. 2. Accordingly, some of the same reference numerals are used herein for easy cross-referencing. Additionally, microfluidic system 800 includes heating/cooling channel 801 disposed in substrate 811, but which is not directly fluidly connected to the channel or chamber in which elevated temperatures are desired. Specifically, this heating channel 801, also termed a heating coil, is disposed in the substrate adjacent to the channel in which elevated temperatures are desired. The heating coil provides thermal energy to channel 421, via conduction and/or convection.

Heating coil 801 includes regions 803 and 805, among others. Coil 801 can be a heating coil or cooling coil, depending upon the application. As a heating coil, coil 801 includes a fluid therein. A voltage is applied between regions 803 and 805 to direct current through the fluid for heating purposes. In particular, a power supply provides a voltage differential between regions 803 and 805. Current flows between 803 and 805 and traverses through a plurality of coils 809 (which can be planar), which are defined in a substrate 811. Shape and size of the coils can influence an ability of current to heat the fluid. As current traverses through the fluid, energy is transferred to the fluid for heating purposes. Heat from the fluid conducts through substrate 811 to channel 421, which is also filled with fluid. Accordingly, fluid in channel 421 conducts heat through the substrate from heating coil 801.

Alternatively, channel 801 can be a cooling coil. As a cooling coil, a fluid traverses from region 805 through coils 809 to region 803. For instance, region 805 can be a source of cooling fluid and region 803 can be a sink for the cooling fluid after traversing through coil 809. Heated fluid in region 407 can be transferred to channel region 421 where fluid is cooled. In particular, heat from the fluid dissipates through walls of channel 421, through substrate 811, to heat sink or cooling fluid in coils 809. Cooling fluid in coils 809 take heat away from fluid in channel region 421 through either region 803 or 805, depending upon the application. The cooling fluid can be a variety of substances including liquids and gases. As merely an example, the cooling fluid includes aqueous solutions and others. The cooling fluid can be moved between regions 803 and 805 using any of the techniques described herein, and others.

As described for the various embodiments set forth above, in combination with heating or cooling, material also moves or is transported between any of the regions described in FIG. 6. For example, fluid or material flows from region 409 to region 411 or in the inverse direction. Fluid also can flow from region 423 to region 425, or the inverse direction. Fluid flow or movement occurs by any of the techniques described herein and others. Of course, the particular combination of fluid movement and heating or cooling depends upon the application.

Figure 7:
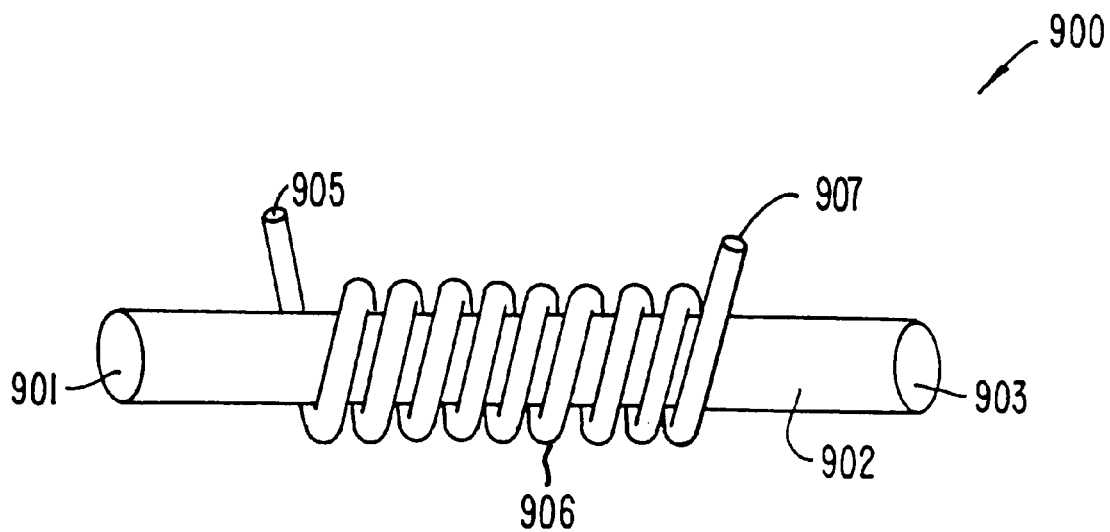
FIG. 7 is a simplified diagram of a microfluidic system with a heating source according to still yet an alternative embodiment of the present invention.

FIG. 7 is a simplified diagram of a microfluidic system with a heating or cooling source according to another alternative embodiment of the present invention. This diagram is merely an illustration and should not limit the scope of the claims herein. One of ordinary skill in the art would recognize other variations, alternatives, and modifications. In this embodiment, microfluidic system 900 includes a variety of features including a channel 902, which has end regions 901 and 903. Fluid or material moves through channel 902 from region 901 to region 903 or in the inverse direction.

As fluid or material moves from either region, fluid can be cooled or heated by way of conduction from heating or cooling coils 906. As heating coils, coils 906 provide high temperature fluid from region 907 to region 905, or in the inverse direction. Although illustrated as a coil surrounding, e.g., coiled around, channel 902, it will be readily appreciated that in preferred aspects, e.g., for microfluidic devices employing a planar structure, the coil will be disposed adjacent to or in a layer above or below the channel 902, whereupon thermal energy from the channel is conducted through the substrate to the channel. Preferably, a power source supplies a voltage differential between regions 905 and 907 for providing electric current to the fluid for heating purposes. The voltage differential is applied to the fluid using a pair of electrodes in contact with the fluid in regions 905 and 907. Heated fluid through coils 906 transfers thermal energy via a temperature gradient to fluid in channel 902. Coils 906 can be defined in a substrate to include coils 906 and channel 902. Alternatively, coils 906 can be made of an independent structure, which is wrapped around channel 902. Coils 906 are preferably close enough to or in contact to channel 902 to transfer thermal energy from fluid in coils 906 to fluid in channel 902. Fluid in coils 906 can be moved using a variety of techniques including those described in this present specification.

As cooling coils 906, cooling fluid traverses through coils 906 to carry away thermal energy in the form of heat from channel 902. Cooling fluid is removed from either region 905 or 907, depending upon the application. Cooling fluid can be moved using a variety of techniques, including those described in this specification. Heat from fluid in channel 902 is removed from the fluid through a substrate, which includes coils 906 and channel 902, to the cooling fluid via a temperature gradient. That is, heat is removed from fluid in channel 902 using a combination of conduction, and convection if necessary.

In combination with heating or cooling fluid in channel 902, fluid moves between region 901 and region 903. In particular, fluid can move or is transferred from region 901 to region 903. Alternatively, fluid can move or is transferred from region 903 to region 901. Fluid movement occurs using any of the techniques described herein and others. Of course, the particular combination of fluid movement and heating or cooling depends upon the application.

Figure 8:
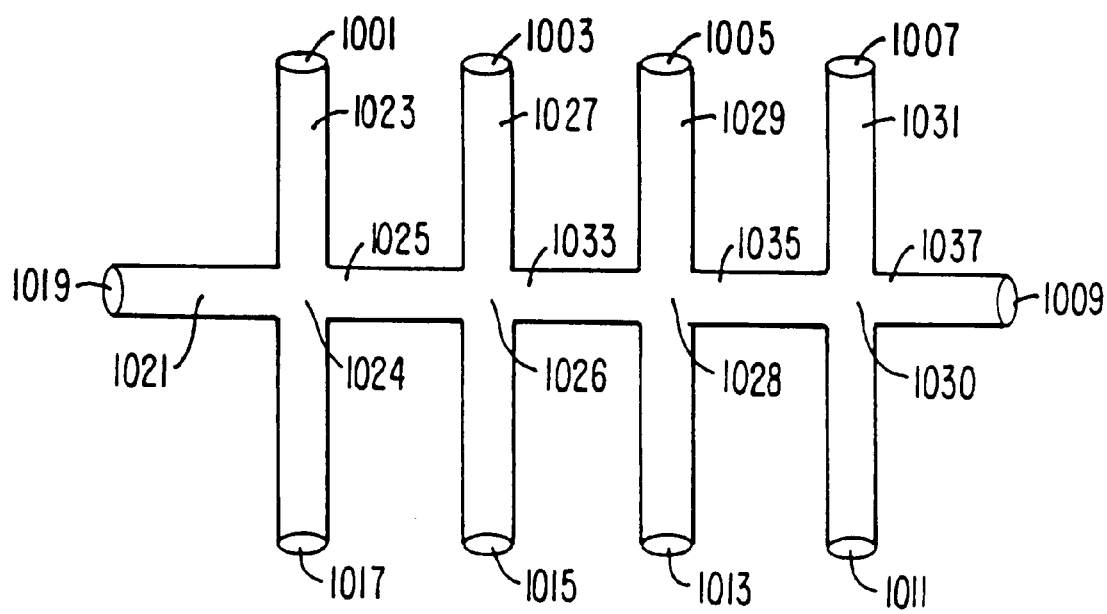
FIG. 8 is a simplified diagram of a microfluidic system with a plurality of heating sources according to the present invention.

In an alternative embodiment, the present invention provides a novel microfluidic system 1000 for successively heating and cooling moving fluid in a channel using multiple heating sources, as shown by FIG. 8. FIG. 8 is merely an illustration and should not limit the scope of the claims herein. One of ordinary skill in the art would recognize other variations, alternatives, and modifications. System 1000 includes a variety of elements including a main channel, including channel regions 1021, 1025, 1033, 1035, and 1037, which extends from end region 1019 to end region 1009. Fluid generally traverses through the main channel from end region 1009 to end region 1019, or in reverse, depending upon the application. Numerous techniques can be used to move fluid through the main channel including those described herein, but can be others. System 1000 also includes a plurality of heating source channels 1023, 1027, 1029, and 1031. Each of these heating channels has at least two end regions. For example, channel 1023 has end regions 1001 and 1017. Channel 1027 has end regions 1003 and 1015. Channel 1029 has end regions 1005 and 1013. Channel 1031 has end regions 1007 and 1011.

Each heating channel also has a region that intersects main channel 1021. For example, channel 1023 intersects with main channel between channel regions 1021 and 1025 at channel region 1024. Channel 1027 intersects with main channel between channel regions 1025 and 1033 at channel region 1026. Channel 1029 intersects with main channel between channel regions 1033 and 1035 at channel region 1028. Channel 1031 intersects with main channel between channel regions 1035 and 1037 at channel region 1030.

In a specific embodiment, heating of fluid occurs at intersection regions 1024, 1026, 1028, and 1030. In particular, a power source (or sources) provides a voltage differential between each of the end regions of at least one of the heating channels to provide current that heats fluid in at least one of the intersection regions, 1024, 1026, 1028, and 1030. For example, a voltage differential between regions 1001 and 1017 causes current to flow through the fluid which heats fluid in region 1024. A voltage differential between regions 1003 and 1015 heats fluid in region 1026. A voltage differential between regions 1005 and 1013 heats fluid in region 1028. A voltage differential between regions 1007 and 1011 heats fluid in region 1030. Voltage applied between any pair of end regions can be the same or different from any other pair of end regions.

Figure 9:
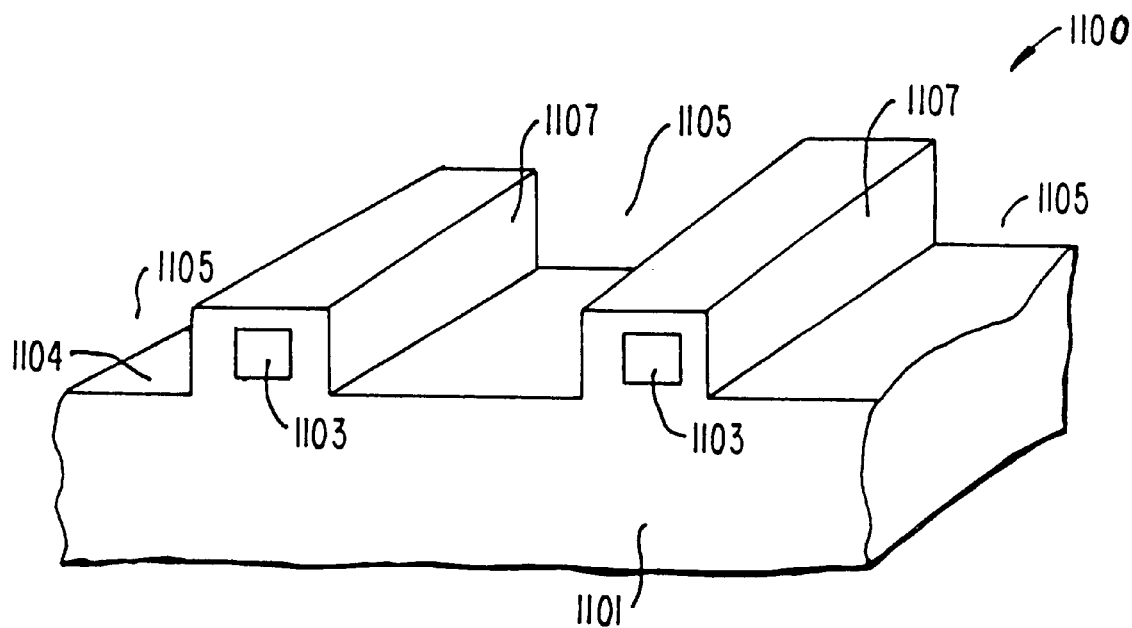
FIGS. 9 and 9A are simplified diagrams of a microfluidic system with heating and cooling sources according to the present invention.

FIG. 9 is a simplified cross-sectional view diagram of an example of a microfluidic channel system 1100 having a cooling source according to the present invention. The diagram is merely an illustration and should not limit the scope of the claims herein. One of ordinary skill in the art would recognize other variations, modifications, and alternatives. Fluid flows through channel 1103, which is defined in section 1107 of substrate 1101 which protrudes outwardly from surface 1104. Fluid in channel 1103 can be heated using any of the techniques described herein. Protruding section 1107 can be made using a variety of techniques such as masking and etching, milling, and others. As shown, protruding section 1107 is shaped as a "fin" to allow for thermal dissipation of heat from fluid in channel 1103 through region 1107 to region 1105 (e.g., ambient, vacuum). Region 1105 is designed to transfer heat away from substrate 1107.

Figure 9A:
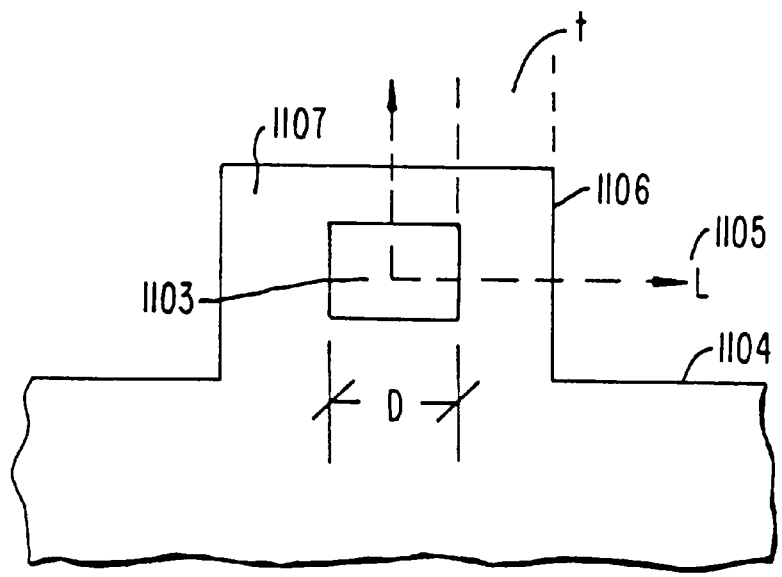

To illustrate the movement of heat in fluid of channel 1103 in the present embodiment, FIG. 9A shows a more detailed diagram of the channel 1103 of FIG. 9. This diagram is merely an illustration and should not limit the scope of the claims herein. Channel 1103 includes a width ("D") and region 1107 has a thickness ("t"). Fluid is heated in channel 1103 by way of a heating source such as electric current applied directly to the fluid along the length of the channel. Removing the electric current from the fluid removes the heating source from the fluid, and heat dissipates out of the fluid via a temperature gradient from the fluid through region 1107 and out to region 1105. An axis ("L") from a center region of channel 1103 moves outwardly toward region 1105.

Figure 10:
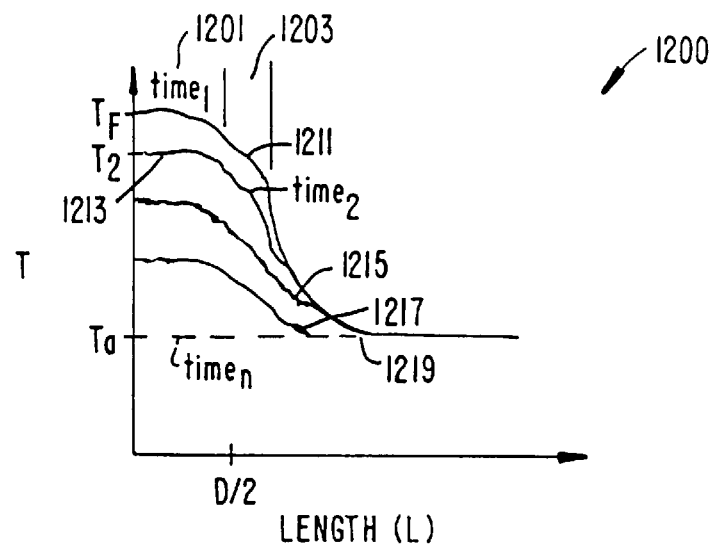
FIG. 10 is a simplified plot of temperature in the microfluidic system of the above Figure.

FIG. 10 is a simplified diagram illustrating a temperature gradient of a heated fluid in channel 1103, as shown by FIG. 9A, for example. Temperature is shown on the vertical axis, and length along axis L is defined on the horizontal axis. The diagram illustrates region 1201, which is fluid in channel 1103 from the center region of channel 1103 to an outer periphery of channel 1103. The diagram also illustrates region 1203, which is defined by the thickness t of region 1107. External region 1105 is defined by reference numeral 1205. The series of line plots 1211, 1213, 1215, 1217, and 1219 represent temperature profiles across the fluid through the channel region, the thickness t, and ambient region 1105 for different times.

Referring to line plot 1211, for example, fluid in channel 1103 has a temperature ("$T_F$"), which is greater than ambient temperature ("$T_a$"), when electric current is applied to the fluid for heating purposes. As electric current is reduced or removed from the fluid in the channel, fluid temperature in the channel drops toward $T_a$, as shown by the arrow and the line plots 1213, 1215, 1217, and 1219. In fact, temperature of the fluid drops continuously from $T_F$ to $T_2$ down to $T_n$, which is also $T_a$. As shown, a temperature gradient from $T_F$ to $T_a$ drives heat out of the fluid in the channel to region 1205 until equilibrium is achieved as referenced to line plot 1219. A similar plot can be made for heating the fluid from ambient temperature to $T_F$ in reference to time.

Although this example is made in reference to region 1105 being at ambient (e.g., air), region 1105 can be filled or be in contact with a variety of fluids or materials to enhance or reduce heat transfer from or to fluid in the channel. For example, region 1105 can be filled or in contact with a highly conductive fluid at a relatively low temperature to further enhance heat transfer from the fluid to region 1105. Additionally, the highly conductive fluid can be flowed over surface 1106 to provide convective forces, which move heat away from fluid in channel 1103. An example of this fluid includes, among others, water, oils. Alternatively, region 1105 can be in contact with or filled with a heating source, which further drives heat into fluid in channel 1103. The type of fluid used depends upon the application.

Although the devices, systems and methods described herein are generally useful in place of more conventional temperature control methods and systems, in certain embodiments, the present invention is used in conjunction with such conventional systems to provide complementary temperature control. Specifically, in many embodiments, it would be desirable to maintain the entire microfluidic system at an elevated temperature, e.g., above ambient. For example, in many thermal cycling operations, e.g., PCR and the like, the base temperature is elevated over typical ambient temperatures. However, power requirements for heating all of the channels of the system using the methods of the invention can be quite high. Accordingly, globally controlling the temperature of the system at the elevated base temperature can be carried out utilizing conventional means, thereby minimizing the control and power requirements of such heating. Such conventional means include common external temperature control systems, such as water baths, ovens, hot plates and the like. Alternatively, integrated global temperature control systems, e.g., integrated into the structure of the microfluidic device, may be utilized. Such systems include resistive heaters, e.g., thin film heaters and heating coils, peltier heaters, and the like.

Figure 11:
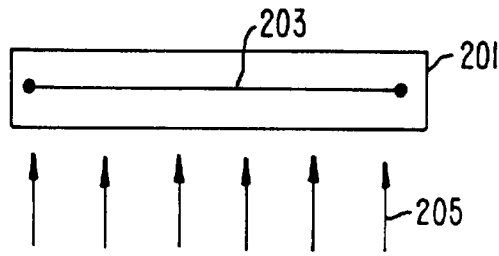
FIG. 11 is a simplified diagram of a microfluidic system with global heating and cooling sources according to the present invention.

FIG. 11 is a simplified diagram of a microfluidic system 200 with an energy source, external to the fluid, used to globally raise and/or lower temperature of the microfluidic device or system, and thereby heat and/or cool fluid or material in the microfluidic system according to the present invention. This diagram is merely an illustration and should not limit the scope of the claims herein.

As shown, the system includes a variety of features such as microfluidic system 200, which has a plurality of channels 203, which are defined on a substrate 201. These channels include fluid or material to be heated or cooled and transported. Fluid can be selectively heated in a specific location in the channel according to any of the techniques described above. Fluid also can be transported or moved within the channel using any of the techniques described herein and others. In certain embodiments, fluid is moved to a specific location in the channel and heated during the same process sequences. In the present embodiment, fluid temperature also is globally raised or lowered during any process or processes as described herein and others.

A variety of methods can be used to globally raise or lower fluid temperature in the microfluidic system, using energy sources or sinks to affect this temperature change. The energy source can be a thermal source, a chemical source, or an electrical source, as well as any other source. The energy sink can be a thermal sink or a chemical sink. The energy source or sink can be flood, time-varying, spatially varying, or continuous. As merely an example, global heating can be supplied by radiation, convection, or conduction. Heat sources can include photon beams, a fluid jet, a liquid jet, an electromagnetic field, a gas jet, an electron beam, a thermoelectric heater, e.g., a peltier device, resistive heaters, e.g., thin film or coil heaters, water baths, or a furnace. The thermal sink can include, among others, a fluid jet, a liquid jet, a gas jet, a cryogenic fluid, a supercooled liquid, a thermoelectric cooling means, e.g., peltier device or an electromagnetic field. The electrical source can be an applied voltage or an applied electromagnetic means. Other types of energy sources can also be used.

Figure 12:
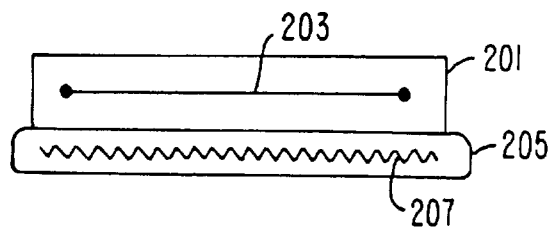
FIG. 12 is a simplified diagram of a microfluidic system with a global heating source according to the present invention.

Global heating or cooling systems can be external, i.e., separate, from the microfluidic device, or alternatively, integrated into the device structure. In preferred aspects, the energy source is a heating element, such as a resistive thin film or coil heater, or peltier heater, that is either external to or integrated within the device. In particular, the heating element is which is placed against a surface or surfaces of the substrate in the microfluidic system, such as the one of FIG. 12. The heating element 205 transfers thermal energy from, e.g., resistive element 207 in the heating element to the microfluidic system by way of conduction. Thermal energy provided to the microfluidic system globally increases temperature of the microfluidic system to a desired temperature. More particularly, electric current, which flows through the heating element, is converted to thermal energy. The thermal energy flows from hotter to cooler regions. Since the resistive element of the heating element is the hottest region, thermal energy flows from the resistive element towards the microfluidic system via conduction. Conduction of thermal energy or heat from the heating element transfers to the surface of the microfluidic system into the substrate. This thermal energy globally increases the temperature of the substrate in the microfluidic system. Accordingly, fluid temperature within the channels and/or chambers of the microfluidic system is also globally increased. An internal controller in the heating element or within the microfluidic device can be used to regulate the temperature of the microfluidic system. Of course, numerous other energy sources can be used to globally raise fluid temperature in the microfluidic system in other applications.

Numerous techniques can be used to control power to the microchannels for the purpose of moving the fluid. These techniques can also be used to selectively monitor and adjust temperature in the microchannels or annular regions, as well. As noted above, one example of one of these techniques is the use of a processor or controller and/or computer software such as the one described above. Alternatively, exclusively hardware or preferably a combination of hardware and software can perform these techniques. Details with regard to specific computer programs that can perform selected techniques according to the present inventions are described below.

In a specific embodiment, the present invention provides a technique used to detect and control temperature of a fluid being heated in a microchannel by way of current and voltage measurements. Depending upon the application, other techniques may also be used. These techniques, of course, depend upon the application. The present technique may be briefly described by way of the following sequence of steps:

(1) Flow fluid in channel of microfluidic system;
(2) Stop flow of fluid in microchannel (optional);
(3) Apply electric current through fluid;
(4) Measure voltage drop across fluid and corresponding electrical current through fluid;
(5) Calculate power dissipated through fluid from voltage drop and electrical current measurement;
(6) Calculate actual temperature of fluid based upon power dissipated through fluid;
(7) Compare actual temperature of fluid based upon a desired temperature set-point;
(8) Adjust electrical current applied to the fluid based upon a difference between the actual temperature and the desired temperature set-point.

Figure 13:
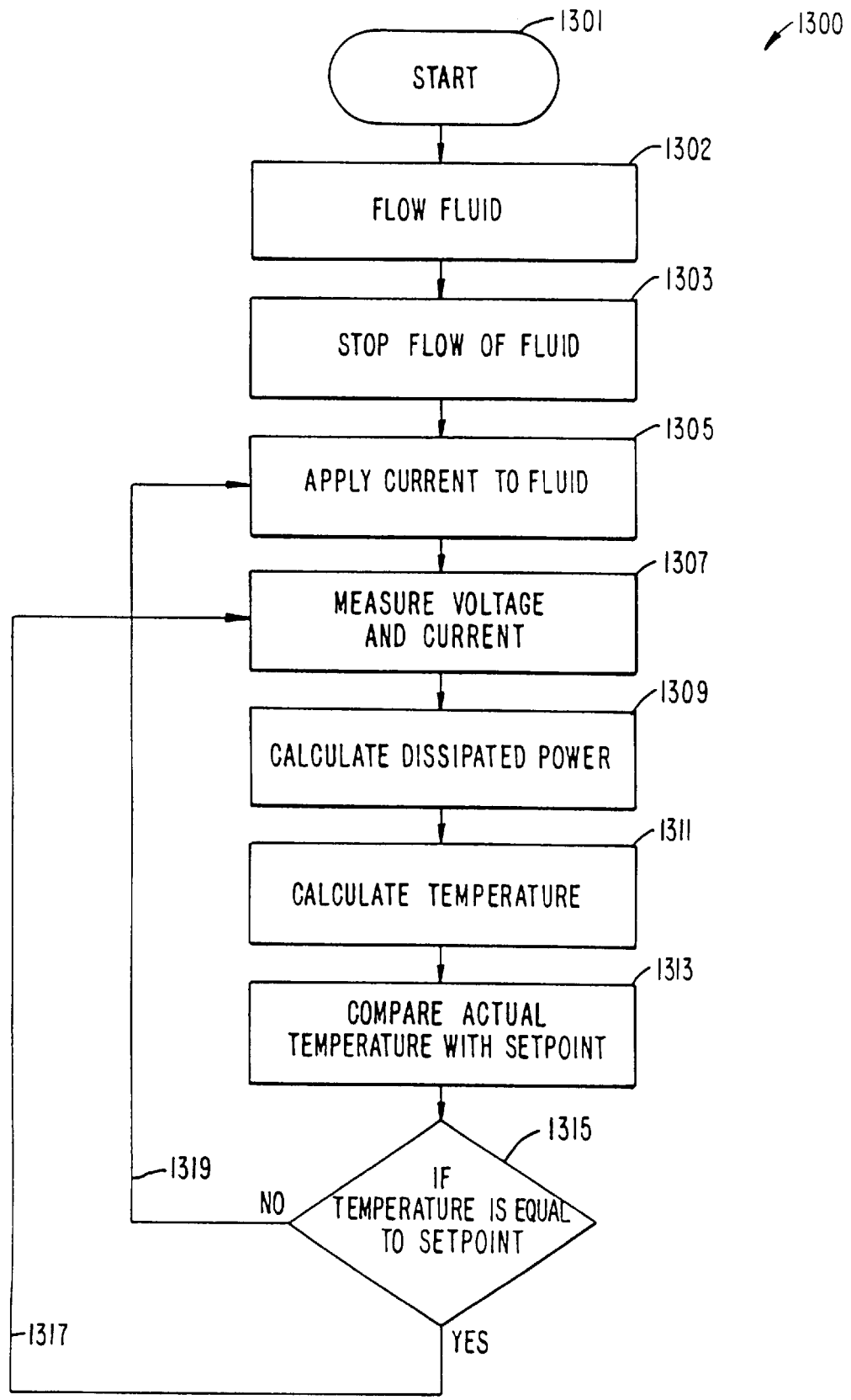
FIG. 13 is a simplified flow diagram of a temperature control and detection method according to the present invention.

The above sequence of steps can be performed using, for example, a computer program. The computer program provides an easy-to-use method to perform the above steps in a microfluidic system. The computer program can be executed in the form of computer software, firmware, hardware, or combinations thereof. The program executes the above functions using an interface that is coupled to the microfluidic system. The interface receives signals from the microfluidic system and provides signals to, for example, the power source, which supplies electric current to fluid for heating purposes. Details of the above sequence of steps are described below in reference to a simplified flow diagram of FIG. 13.

A process 1300 according to an embodiment of the present invention begins with step 1301, which generally requires the use of a microfluidic system such as those described herein and others. The process flows fluid (step 1302) into a microchannel or capillary by way of electroosmotic and/or electrophoretic forces, but are not limited to these forces. These forces are described throughout the present specification, but are not limited. The fluid can be controlled by way of a controller or computer. Optionally, fluid flow slows, increases, or stops in the channel (step 1305) by way of selectively applying energy to the fluid through the controller. Alternatively, fluid flow can remain at a constant flow in the channel.

To heat the fluid in the channel, electric current is applied to the fluid (step 1305) by way of, for example, electrodes coupled directly to the channel. The controller or computer provides a signal to turn-on a power supply to provide current directly to the electrodes. Upon applying electric current, fluid heats in the channel or a selected region of the channel having a smaller inner periphery. The electric current can be DC, AC, or pulsed, depending upon the application. A controller or computer can be coupled to the power supply to identify a voltage and a current applied to the fluid as shown in step 1307.

The amount of voltage and current can be converted into power being dissipated into the fluid. Based upon the type of fluid, temperature is calculated (step 1311). For example, fluid temperature can be found in look-up tables. These calculations can be performed by, for example, computer software programs on a controller or computer.

The controller or more properly a computer program compares (step 1313) the actual temperature from the calculation to a desired set-point temperature, which is previously stored in memory of the computer. Depending upon the difference between the actual temperature and the set-point, current may be added to the fluid or reduced using the controller (e.g., switches). For example, if the temperature of the fluid is equal to the set-point (step 1315), the process cycles back to step 1307 via branch 1317. Alternatively, the method provides adjustment (e.g., increase, decrease) to current to the fluid via branch 1319. This sequence of steps can be repeated indefinitely as required by the application.

In a modification to the preceding embodiment, the global or overall temperature of the microfluidic system can be raised or lowered during any one of the above process steps. Overall fluid temperature is preferably globally raised or lowered using the technique described above, but can be others. Accordingly, fluid can be moved from one region to another in the microfluidic system. Fluid movement can be combined with selective heating of the fluid at a selected portion of a microchannel and/or global fluid heating of the entire microfluidic system. Additionally, the fluid in the microfluidic system can be static and heated globally or selectively in a specific location of the microfluidic system.

In an alternative aspect of the invention, a technique for controlling and detecting temperature of a fluid in a microchannel by way of a resistance measurement is provided. Depending upon the application, other techniques may also be used. These techniques, of course, depend upon the application. The present technique may be briefly described using the following steps:

(1) Flow fluid in channel of microfluidic system;
(2) Stop flow of fluid in microchannel (optional);
(3) Apply electrical current to fluid to heat fluid in microchannel;
(4) Measure resistance (or conductivity) of heated fluid in channel;

(5) Calculate actual temperature of fluid based upon measured resistivity (or conductivity);

(6) Compare actual temperature of fluid based upon a desired temperature set-point; and (7) Adjust electrical current applied to the fluid based upon a difference between the actual temperature and the desired temperature set-point.

Figure 14:
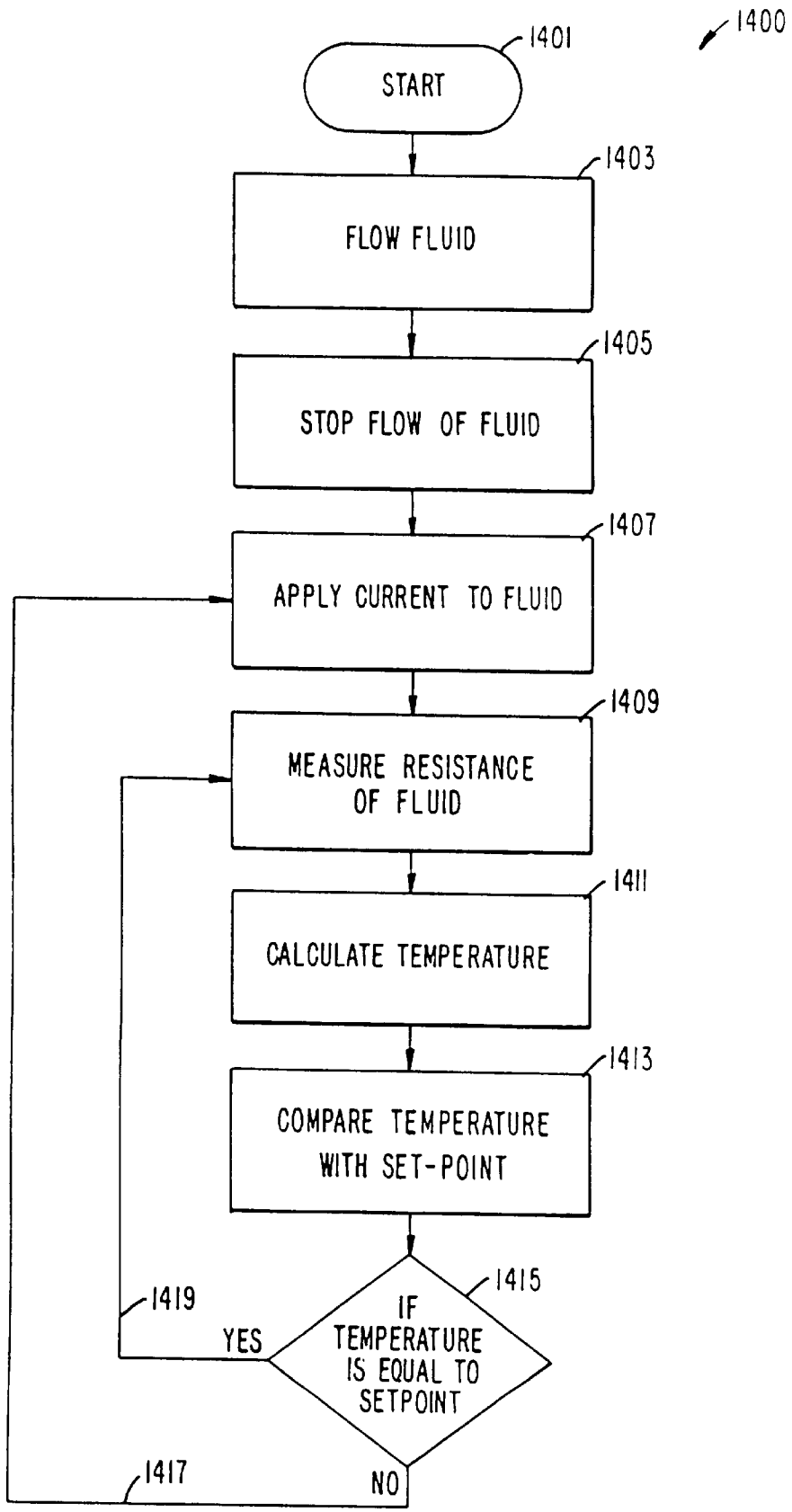
FIG. 14 is a simplified flow diagram of an alternative temperature control and detection method according to the present invention.

The above sequence of steps can be performed using, for example, a computer program. The computer program provides an easy-to-use method to perform the above steps in a microfluidic system. The computer program can be executed in the form of computer software, firmware, hardware, or combinations thereof. The program executes the above functions using an interface that is coupled to the microfluidic system. The interface receives signals from the microfluidic system and provides signals to, for example, the power source, which supplies electric current to the fluid for heating purposes. Details of the above sequence of steps are described below in reference to FIG. 14.

A process 1400 according to the present invention begins with step 1401, which generally requires the use of a microfluidic system such as those described herein and others. The process flows fluid (step 1403) into a microchannel or capillary by way of electroosmotic and/or electrophoretic forces. These forces are described throughout the present specification, but is not limited, e.g., hydrodynamic. The fluid can be controlled by way of a controller or computer. Optionally, fluid flow slows, increases, or stops in the channel (step 1405) by way of selectively applying energy to the fluid through the controller. Alternatively, fluid flow can remain at a constant flow in the channel.

To heat the fluid in the channel, electric current is applied to the fluid (step 1407) by way of, for example, electrodes coupled directly to the channel. The controller or computer provides a signal to turn-on a power supply or energy source to provide current directly to the electrodes. Upon applying electric current, fluid heats in the channel or a selected region of the channel having, for example, a smaller inner periphery. The electric current can be DC, AC, or pulsed, depending upon the application. A controller or computer can be coupled to the fluid via the electrodes or probes to measure resistance or conductivity of the fluid as shown in step 1409.

The measured resistivity can be converted into temperature of the fluid. Based upon the type of fluid, temperature is calculated (step 1411). For example, fluid temperature can be found in a look-up table. These calculations can be performed by, for example, computer software programs on a controller or computer.

The controller or more properly a computer program compares (step 1413) the actual temperature from the calculation to a desired set-point temperature, which is previously stored in memory of the computer. Depending upon the difference between the actual temperature and the set-point, current may be added to the fluid or reduced by using the controller. For example, if the temperature of the fluid is equal to the set-point (step 1415), the process cycles back to step 1409 via branch 1419. Alternatively, the process provides an adjustment in current to the fluid by cycling back to step 1407 via branch 1417. This sequence of steps can be repeated indefinitely as required by the application.

In a modification to the preceding embodiment, the global or overall temperature of the microfluidic system can be raised or lowered during any one of the above process steps. Overall fluid temperature is preferably globally raised or lowered using the technique described above, but can be others. Accordingly, fluid can be moved from one region to another in the microfluidic system. Fluid movement can be combined with selective heating of the fluid in at a selected portion of a microchannel and/or global fluid heating of the entire microfluidic system. Additionally, the fluid in the microfluidic system can be static and heated globally or selectively in a specific location of the microfluidic system.

In an alternative embodiment, temperature of the fluid is detected in the microchannel using fluorescent materials according the present invention. The method may be briefly outlined as follows:

(1) Provide fluid having a tracer material in channel of microfluidic system;

(2) Apply electrical current to fluid to heat fluid in microchannel;

(3) Measure optical property (e.g., intensity) of fluid having tracer material in channel;

(4) Correlate optical property to standards;

(5) Determine actual temperature of fluid based upon optical property;

(6) Compare actual temperature of fluid to desired set-point;

(7) Adjust electrical current applied to the fluid based upon a difference between the actual temperature and the desired temperature set-point.

Figure 15:
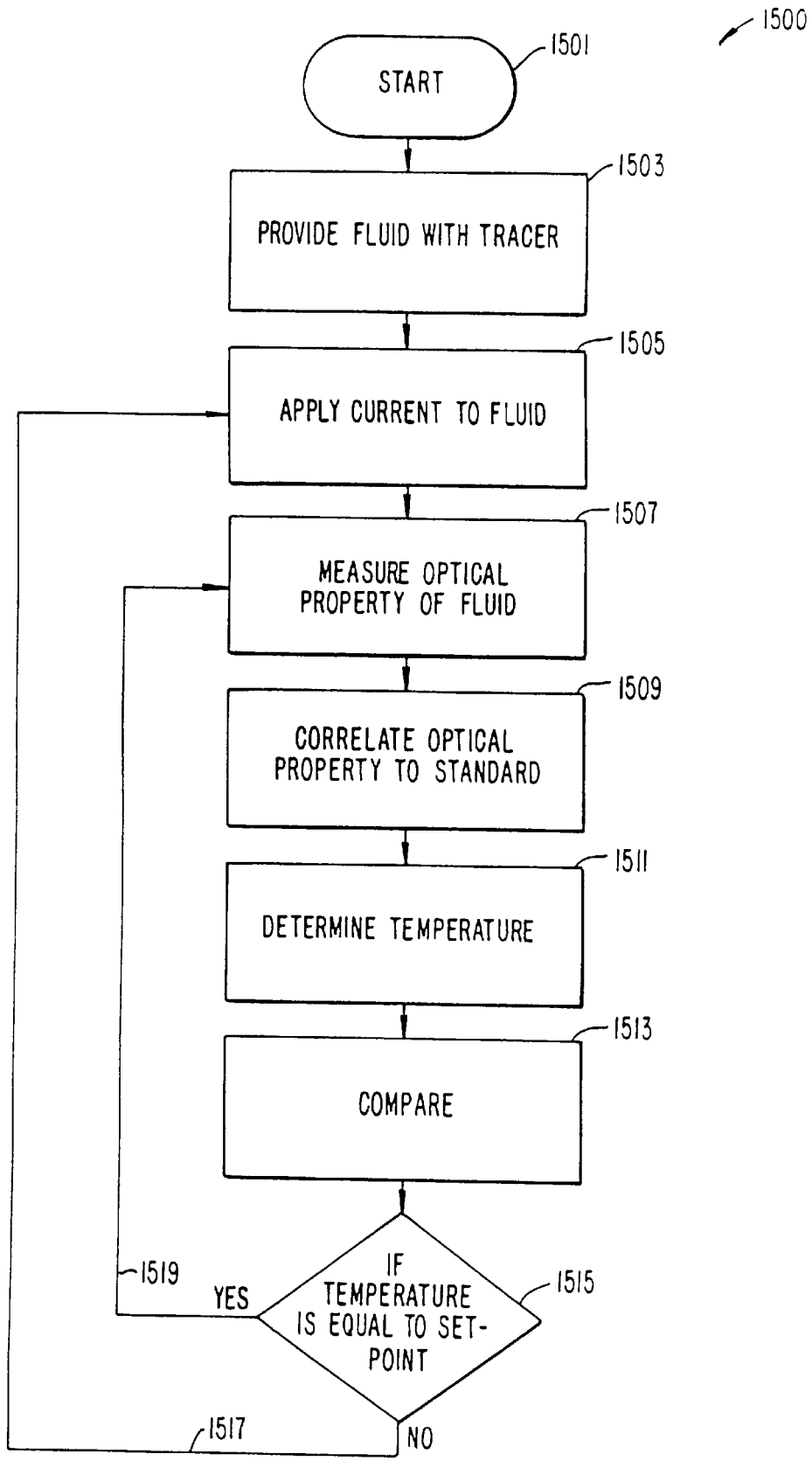
FIG. 15 is a simplified temperature control and detection method using tracer materials according to the present invention.

The above sequence of steps can be performed using, for example, a computer program. The computer program provides an easy-to-use sequence of steps to perform the above steps in a microfluidic system. The computer program can be executed in the form of computer software, firmware, hardware, or combinations thereof. The program executes the above functions using an interface that is coupled to the microfluidic system. The interface receives signals from the microfluidic system and provides signals to, for example, the power source, which supplies electric current to fluid for heating purposes. Details of these steps are described below in reference to the simplified diagram of FIG. 15.

A process 1500 according to the present invention begins with step 1501, which generally requires the use of a microfluidic system such as those described herein and others. The process provides within these systems fluid with a tracer therein, as shown in step 1503. The tracer generally emits light in a manner that is proportional to the temperature of the tracer. More particular, the tracer emits light in proportion to the temperature of the fluid. An example of this tracer is a temperature sensitive fluorescent dye. Of course, the type of tracer used depends upon the application.

A power source applies current (step 1505) to the fluid to heat the fluid in the channel. The electric current is applied to the fluid using, for example, electrodes coupled directly to the fluid in the channel. In particular, the controller or computer provides a signal to turn-on the power supply or energy source to provide the current directly to the electrodes. Upon applying electric current, fluid heats in the channel or a selected region of the channel having a smaller inner periphery. The electric current can be DC, AC, or pulsed, depending upon the application.

A sensor measures a property (e.g., an optical intensity such as fluorescence) (step 1507) of the fluid. In particular, the tracer emits a certain amount of light, depending upon its temperature. The sensor reads the intensity level of light emitted from the tracer. In a preferred embodiment, the sensor is an optical sensor. Alternatively, the sensor can be a CCD (charge coupled device) device or even a CCD camera or the like, which has an array of CCD elements. A light intensity value captured by the sensor is transmitted as an electrical signal to the controller or computer.

The controller correlates the intensity value to standards (step 1511) to determine (step 1509) the actual temperature of the fluid. Correlation occurs, for example, by way of the computer program run by the controller or computer. Of course, there are other ways of determining the actual temperature of the fluid using the measured intensity value (s).

The controller or more properly a computer program compares (step 1513) the actual temperature with a desired set-point temperature, which is previously stored in memory of the computer. Depending upon the difference between the actual temperature and the set-point, current may be added to the fluid or removed using the controller. For example, if the temperature of the fluid is equal to the set-point (step 1515), the process cycles back to step 1507 via branch 1519. Alternatively, the process provides additional current to the fluid by cycling back to step 1505 via branch 1517. This sequence of steps can be repeated indefinitely as required by the application.

The embodiments directed to controlling temperature of fluid can be further modified or controlled by way of an active feedback process or control, depending upon the application. The active feedback process generally receives a signal such as temperature from the microfluidic process, for example. The actual temperature is compared with a set-point temperature and a difference is calculated. If the actual temperature is less than the set-point, a result based upon a function of the temperature difference is used to provide additional current or voltage to the fluid for heating purposes. In preferred embodiments, the function prevents any substantial "overshoot" or "oscillation" of the actual temperature from the set-point temperature. Additionally, the function ensures that the set-point is achieved in an efficient manner. Examples of functions used to provide feedback control include among others, proportional control, differential control, integral control, or a combination thereof.

Using, for example, proportional control, a feedback process according to the present invention provides an active feedback to the process based upon a multiplier. An output of a proportional controller is a fixed multiple of a measured difference or "error." That is, the proportional controller is simply the multiplier. Terms often used in describing proportional controllers include a proportional band and a controller gain. Controller gain is an amount by which the error is multiplied to obtain an output. The controllers can be calibrated to the proportional band rather than the gain depending upon the application.

A process according to the present invention generally measures a signal such as these described above for identifying a temperature of the fluid. The signal is transduced. The transduced signal is compared with a desired set-point. A difference between the transduced signal and signal corresponding to the desired set-point is calculated. The difference is amplified by a constant, which is the proportional gain. The amplified difference provides an output, which drives current to reduce the difference. This example is merely an illustration and should not limit the scope of the claims herein.

In a modification to the preceding embodiment, the global or overall temperature of the microfluidic system can be raised or lowered during any one of the above process steps. Overall fluid temperature is preferably globally raised or lowered using the technique described above, but can be others. Accordingly, fluid can be moved from one region to another in the microfluidic system. Fluid movement can be combined with selective heating of the fluid in at a selected portion of a microchannel and/or global fluid heating of the entire microfluidic system. Additionally, the fluid in the microfluidic system can be static and heated globally or selectively in a specific location of the microfluidic system.

Although the embodiments described above are in terms of controlling temperature of the fluid by measuring actual temperature, the temperature can also be controlled by simply setting the current or the voltage or power applied to the fluid by way of the power supply. For example, the power supply can be operated in a current controlled mode such that the amount of current applied to the fluid remains constant and voltage varies depending upon any changes or fluctuations in resistance of the fluid. Alternatively, voltage of the power supply can remain constant while current is varied depending upon any changes or fluctuations in resistance of the fluid. Still further, the power supply can be operable in a mode where a combination of current and voltage remains constant, depending upon the application. Of course, the mode used depends upon the application.

Although the above descriptions are in terms of flow diagrams, which can be carried out with computer software, the present inventions can also be carried out in many other ways. For instance, the computer software can be placed in hardware such as a memory device, e.g., field programmable gate arrays ("FPGAs"), electrically erasable programmable read only memories ("EEPROMs"), read only memories ("ROMs"), random access memories ("RAMs"), etc. Another type of memory device would be a compact disk read only memories ("CDROMs"), hard disks, floppy disks, high capacity disks (e.g., ZipDrive™ sold by Iomega Corporation), and others. Alternatively, the computer software can be placed in a combination of hardware and software. Some of the functions described can be separated, or even combined, depending upon the application. Of course, one of ordinary skill in the art would recognize other variations, modifications, and alternatives, depending upon the particular application.

III. Process Monitoring Embodiments Using Conductivity

In a specific embodiment, the present invention provides techniques for monitoring a variety of process parameters such as concentration of species in the fluid or material, pH, temperature, and the like More particularly, these parameters can be found by measuring fluid conductivity. That is, a fluid conductivity measurement is correlated to a fluid parameter such as fluid concentration, pH, temperature, and such parameter is compared to a desired parameter set-point. These techniques may be used alone, or in combination with the heating applications and/or material transport systems described above. A method according to the present embodiment may be briefly outlined as follows:

(1) Provide fluid in channel of microfluidic system;

(2) Measure conductivity of fluid in channel of microfluidic system;

(3) Correlate measured conductivity to standard parameter values such as fluid concentration, pH, or temperature in a look-up table;

(4) Compare value of fluid parameter from look-up table against a set-point value; and (5) Perform adjustments to process as needed.

Figure 16:
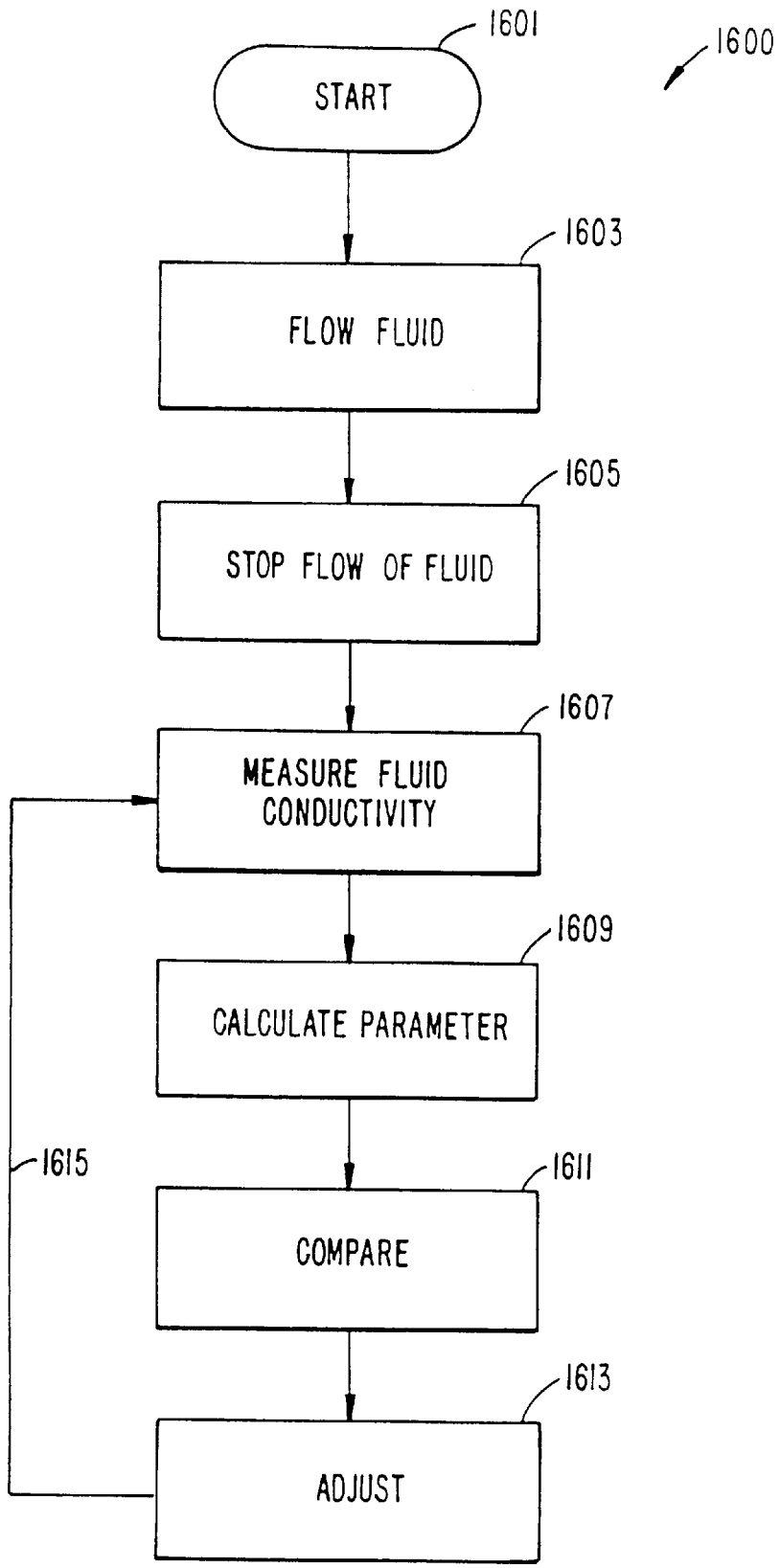
FIG. 16 is a simplified flow chart of monitoring a process parameter according to the present invention.

The above sequence of steps can be performed in the present microfluidic system. A program executes the above functions using at least an interface that is coupled to the microfluidic system. The interface receives signals from the microfluidic system, which correspond to conductivity values, and provides signals as intensity values to a controller. The controller reads the intensity value or values and determines the actual parameter value or values based upon, for example, a look up table or the like. Details of these steps are described below in reference to the simplified diagram of FIG. 16.

A process 1600 according to the present invention begins with step 1601, which generally requires the use of a microfluidic system such as those described herein and others. The process flows fluid (step 1603) into a microchannel or capillary by way of electroosmotic and/or electrophoretic forces. These forces are described throughout the present specification, but are not limited, e.g., hydrodynamic. The fluid can be controlled by way of a controller or computer. Optionally, fluid flow slows, increases, or stops in the channel (step 1605) by way of selectively applying energy to the fluid through the controller. Alternatively, fluid flow can remain at a constant flow in the channel. To determine fluid conductivity, a controller or computer coupled to the fluid via the electrodes or probes measures resistance or conductivity of the fluid, as shown in step 1609.

The measured resistivity or conductivity can be converted into fluid concentration, pH, temperature or other fluid characteristics or parameters. Based upon the type of fluid, selected fluid parameters are calculated (step 1611). For example, the selected fluid parameter can be determined or calculated by way of a look-up table or tables. These calculations can be performed by, for example, by computer software programs on a controller or computer.

The controller, or more properly, a computer program, compares (step 1613) the measured or calculated fluid parameter to a desired set-point, which is previously stored in memory of the computer. Depending upon the difference between the measured fluid parameter and the set-point, the measured parameter or other parameters in the system may be adjusted, step 1615. Alternatively, the system may be shut down temporarily to reset certain parameters. Additional conductivity valves are measured via branch 1617.

As merely an example, conductivity of a buffer fluid determines the type of buffer and pH value. The conductivity of the buffer is a function of acid/salt concentration, pH and temperature. Additionally, the conductivity may also be utilized to determine the contents of the buffer solution, as well as other features. A buffer consisting of 1 M Sodium acetate buffer (NaOAc) at pH 5 made with hydrochloric acid (HCl) (e.g., 1M NaOAc adjusted to pH 5 by adding HCl) has a specific conductivity that is higher than a 1 M NaOAc buffer at pH 5 made with sodium hydroxide (NaOH) (e.g., 1M acetic acid (HOAc), adjusted to pH 5 by adding NaOH).

By way of these specific and unique inherent characteristics in numerous buffer solutions, a look-up table of conductivity values for commonly used buffers as a function of, for example, concentration, pH, temperature, can be made and used to identify the buffer fluid being measured and used in the microfluidic system, or as a quality assurance mechanism to ensure that the proper buffers are being utilized in the system. Specific values for given buffers can be readily determined by routine experimentation.

These values are then optionally incorporated into a look-up table for a variety of commonly used buffer solutions. The look-up table typically lists commonly used buffers in one column. Concentration, pH, and temperature are listed in second, third, and fourth columns, respectively. This look-up table may be stored in memory of a computer or controller for easy access. Accordingly, the present invention allows the user of the microfluidic system to identify and determine a number of parameters by way of a measured fluid conductivity value.

Numerous benefits are achieved by way of monitoring process parameters according to the present invention. For example, the user of the microfluidic system can easily determine whether the proper fluid is being used in a selected microchannel by way of a simple conductivity measurement, which will be correlated to a variety of inherent fluid parameters or characteristics. Additionally, the present invention allows the user to have greater confidence in the data being generated in the microfluidic system, which is often difficult to monitor using conventional tools and monitoring equipment. Furthermore, the present invention provides for "high quality" data, which can be shown to a potential customer of the data. Moreover, the present invention provides a technique for in-situ process monitoring by way of simple conductivity measurements. Accordingly, the in-situ monitoring technique can provide the user with greater "confidence" in the results of the operation being performed.

In a modification to the previous embodiment, fluid can be selectively heated during the process monitoring step or steps. A power supply providing electric current through the fluid selectively heats a portion or portions of the fluid in the microchannel. Any of the techniques described herein and others can be used to heat the fluid. The fluid can even be cooled by way of the techniques described herein using the present monitoring techniques. Accordingly, fluid can be selectively cooled and heated in combination with the present monitoring technique.

In a further modification to the preceding embodiment, the global or overall temperature of the microfluidic system can be raised or lowered during any one of the above process steps. Overall fluid temperature is preferably globally raised or lowered using the technique described above, but can be others. Accordingly, fluid can be moved from one region to another in the microfluidic system. Fluid movement can be combined with selective heating of the fluid in a selected portion of a microchannel and/or global fluid heating of the entire microfluidic system. Additionally, the fluid in the microfluidic system can be static and heated globally or selectively heated in a specific location of the microfluidic system.

Although the above descriptions are in terms of flow diagrams which can be carried out with computer software, the present inventions can also be carried out in many other ways. For instance, the computer software can be placed in hardware such as a memory device, e.g., field programmable gate arrays ("FPGAs"), electrically erasable programmable read only memories ("EEPROMs"), read only memories ("ROMs"), random access memories ("RAMs"), etc. Another type of memory device would be a compact disk read only memories ("CDROMs"), hard disks, floppy disks, high capacity disks (e.g., ZipDrive™ sold by Iomega Corporation), and others. Alternatively, the computer software can be placed in a combination of hardware and software. Some of the functions described can be separated, or even combined, depending upon the application. Of course, one of ordinary skill in the art would recognize other variations, modifications, and alternatives, depending upon the particular application.

IV. Amplifying and Detecting Nucleic Acids

In a specific embodiment, the present invention relates to processes for the treatment of nucleic acid material in order to effect a complete or partial change from double stranded form to single stranded form and to processes of amplifying or detecting nucleic acids involving such denaturation processes. Preferably, the processes for treatment of nucleic acid material occurs by successively changing temperature of the nucleic acid material by way of thermal cycling. Thermal cycling in accordance with the present invention occurs by applying current to the nucleic acid material in the microcapillary of the microfluidic system. The present invention applies current to the nucleic acid material using any of the techniques described herein, but are not limited to such techniques.

Double stranded DNA, commonly termed "deoxyribonucleic acid" and DNA/RNA, and RNA/RNA complexes in the familiar double helical configuration are stable molecules that, in vitro, require aggressive conditions to separate the complementary strands of the nucleic acid. Methods that are typically employed for strand separation require the use of high temperatures of at least 60° Celsius and often 100° Celsius or more or use an alkaline pH of 11 or higher. The present invention provide methods for obtaining the high temperatures often required for strand separation.

Details of strand separation is described in, for example, U.S. Pat. No. 4,683,202 to Mullis et al. Mullis et al. discloses a process for amplifying and detecting a target nucleic acid sequence contained in a nucleic acid or mixture thereof by separating the complementary strands of the nucleic acid, hybridizing with specific oligonucleotide primers, extending the primers with a heat stable polymerase to form complementary primer extension products and then using those extension products for the further synthesis of the desired nucleic acid sequence by allowing hybridization with the specific oligonucleotide primers to take place again.

The process can be carried out repetitively to generate large quantities of the required nucleic acid sequence from even a single molecule of the starting material. Separation of the complementary strands of the nucleic acid is achieved preferably by thermal denaturation in successive cycles, since only the thermal process offers simple reversibility of the denaturation process to reform the double stranded nucleic acid, in order to continue the amplification cycle. According to the present invention, thermal denaturation in successive cycles occurs by way of successively heating a region of the channel using the techniques described herein. Since the region being heated is for a small volume of fluid, heating and cooling occurs at a sufficient speed or rate to effectively perform the denaturation process.

A technique for thermal denaturation in successive cycles according to the present invention may be briefly outlined as follows:

(1) Provide nucleic acid material into channel;
(2) Apply electric current to fluid to increase temperature of nucleic acid material to first temperature;
(3) Remove electric current from fluid to decrease temperature of nucleic acid material to second temperature; and
(4) Repeat steps 2 and 3 successively until complete.

The above sequence of steps provides for successive thermal cycles in a regional area of a channel. This allows for efficient thermal transfer of heat to the fluid itself, which allows for efficient heating and cooling of the nucleic acid material. Additionally, the present invention provides regional heating of the material itself, and it may not generally require the use of special heat resistant polymerase enzymes from thermophilic organisms for, steps such as, for example, a primer extension step if the continuous addition of heat labile enzyme is to be avoided.

Furthermore, since heat is applied to selected regions of the channel, destruction of the DNA structure itself from broken phosphodiester bonds, for example, at high temperatures is limited. Moreover, the present invention provides for heating (e.g., 90° Celsius and greater) the nucleic acid material in the enclosed volume of a channel, which substantially prevents evaporation of liquid often associated with previously used techniques. Still further, the present invention allows for reactions to occur in very small volumes to provide, for example, reagent economy in applications such as the Human Genome sequencing project and in routine diagnostics industry where reagent economy, where the design of assay format and the speed of the DNA denaturation/renaturation process are important.

The PCR process described above is not intended to be limiting. The PCR process is also described in e.g., U.S. Pat. Nos. 4,683,195; 4,683,202; and 4,965,188; PCR Technology: Principles and Applications for DNA Amplification (ed. Erlich, Freeman Press, New York, N.Y., 1992); PCR Protocols: A Guide to Methods and Applications (eds. Innis et al., Academic Press, San Diego, Calif. (1990); Mattila et al. Nucleic Acids Res. 19:4967 (1991); Eckert & Kunkel PCR Methods and Applications 1:17 (1991); PCR (eds. McPherson et al., IRL Press, Oxford) (each of which is incorporated by reference in its entirety for all purposes). Reagents, apparatus, and instructions for using the same are commercially available. Other amplification systems include the ligase chain reaction, QB RNA replicase and RAN-transcription-based amplification systems.

The present invention is further illustrated with reference to the following nonlimiting examples.

EXAMPLES

Example 1—Thermal Denaturation/Renaturation of Nucleic Acids

To prove the principle and operation of the embodiments of the present invention, experiments can be performed. These experiments are merely examples of many which may be used to show the usefulness and effectiveness of the present invention. Accordingly, these experiments should not limit the scope of the claims described herein. One of ordinary skill in the art would recognize other variations, modifications, and alternatives. An example of a particularly useful application of the methods and systems of the present invention is in the treatment of nucleic acid material in order to completely or partially change from double stranded form to single stranded form and to processes of amplifying or detecting nucleic acids involving these types of denaturation processes.

This experiment was performed to illustrate thermal denaturation of nucleic acids by heating cycles according to the present invention. The nucleic acid is heated in a microchannel, which has a length of about 5 mm and a dimension of about 70×10 $\mu$m, and is rectangular in cross-section. The microchannel is defined in a substrate made of glass, but is not limited to such a material. The channel is similar to the one illustrated by way of FIG. 1, for example. Fluid containing nucleic acid was introduced into the microchannel using the fluid movement techniques described herein. The nucleic acid in this experiment included DNA sequences GACACAGCTACTCCT and AGGAGTAGCTGTGTC. An intercalating dye was added to the fluid to provide a fluorescent signal, depending upon whether the nucleic acid was double stranded or denatured, e.g., melted apart. That is, a fluorescent signal from the intercalating dye is greater when the nucleic acids are double stranded, and less when the nucleic acids are denatured. In this experiment, the intercalating dye is a product sold under the tradename of SyberGreen™, which is manufactured by Molecular Probes, Inc., Eugene, Oreg. Other types of dyes can also be used depending upon the application.

Figure 17:
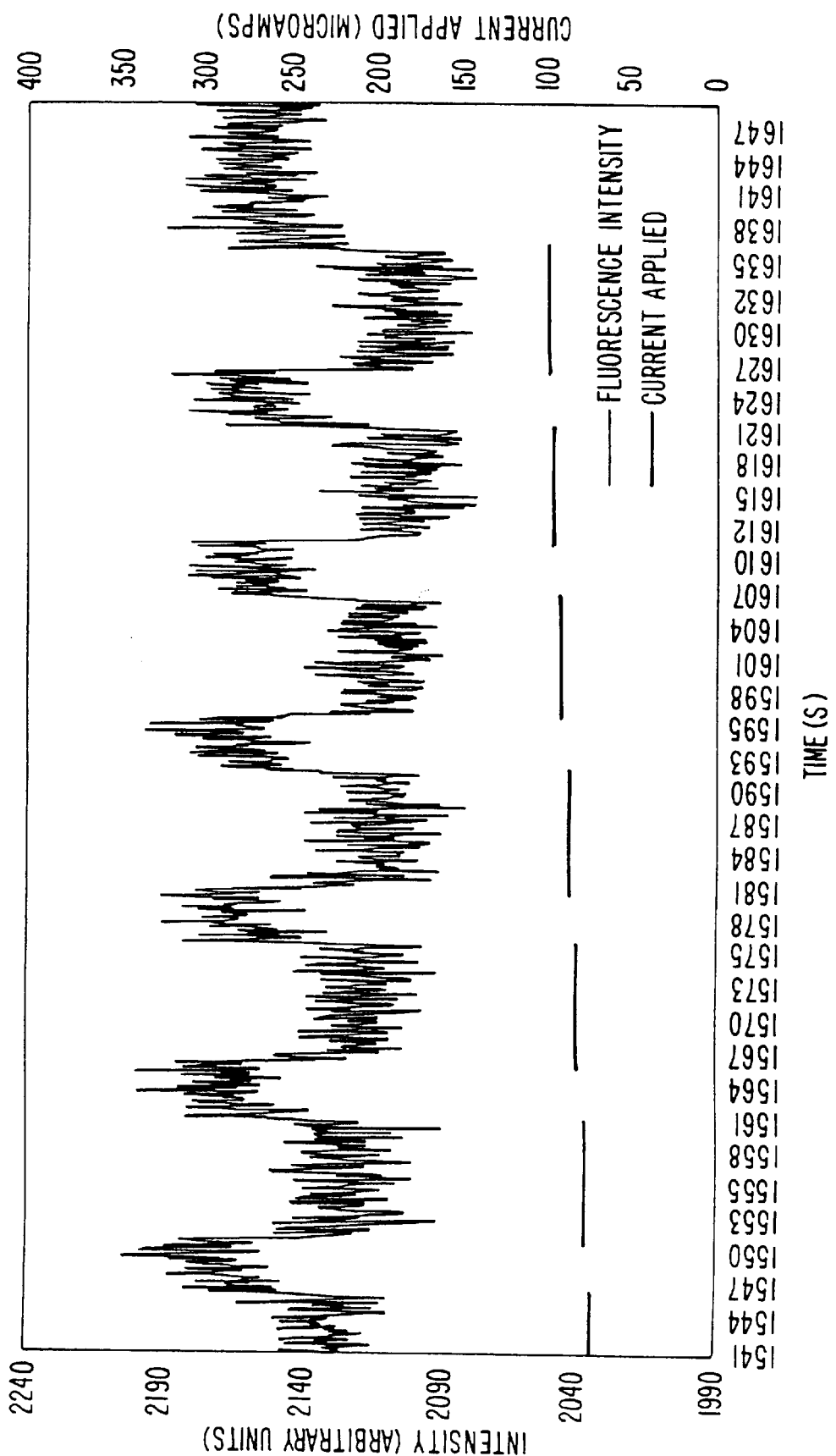
FIG. 17 is a simplified plot of experimental results for thermal cycling a nucleic acid material according to the present invention.

As noted, fluid containing the DNA and the dye was introduced into the channel of the substrate in the microfluidic system. Current was applied to the channel, which caused the intensity of the fluorescent signal to decrease. As current was removed, the intensity of the fluorescent signal increased. FIG. 17 shows a simplified relationship between the intensity of the fluorescent signal and time according to the present experiment. This Figure is merely an illustration and should not limit the scope of the claims herein. As shown, the vertical axis represents intensity, as measured in some arbitrary units. Intensity is generally positive and increases along the positive length of the vertical axis. The horizontal axis represents time, which generally relates to selected periods when current was applied to the fluid for heating purposes. The dashed lines near the bottom portion of the Figure represent times when current was applied to the fluid and the magnitude of the electric currents is indicated on the vertical axis on the right hand side of the Figure.

The measurements indicated that intensity decreased when current was applied to the fluid, which indicates that the DNA in the fluid changed from double stranded to single stranded. As current was removed from the fluid, intensity decreased, which tends to indicate that the DNA in the fluid was converted from single stranded to double stranded DNA, e.g., reannealed. Melting temperature of DNA in this experiment was about 46° C. in a solution of 500 mM borate. The cyclic nature of the changing fluorescent signal indicates that a reversible denaturation of DNA from single to double strand is possible by way of the present invention. Accordingly, the present invention provides for selective heating and cooling of fluid containing DNA, which can be used in a variety of reactions.

Although the above experiment was described generally in terms of successively heating and cooling a specific type of nucleic acid material, the type of nucleic acid material is intended to be limiting. For example, the nucleic acid material can be almost any type capable of being heated and cooled for a variety of reactions such as, for example, PCR, LCR, and others.

Depending upon the application, the present invention provides fluid having one of many flow and temperature characteristics in the channel of a microfluidic system. In a specific embodiment, the fluid moves through the channel at a relatively constant temperature, which is not adjusted by way of a heating source. Alternatively, fluid moves through the channel at an elevated temperature throughout the length of the channel or in a specific region of the channel, which is often dependent upon the geometric shape of the specific region. Alternatively, fluid moves into the channel and then stops in the channel, and is heated completely or partially by way of the present embodiments. Alternatively, fluid moves at varying rates through the length of the channel. Temperature of the fluid can also be heated and/or cooled throughout the channel or at a specific region of the channel. Of course, the flow and temperature characteristic of the channel will depend highly upon the application, e.g., PCR, LCR, and others.

In a related example, thermal control of nucleic acid melting and reannealing is carried out utilizing applied currents. In this example, a molecular beacon consisting of a fluorescent donor-acceptor pair coupled to opposite ends of a self-hybridizing nucleic acid sequence is used. The molecular beacon self-hybridizes placing the donor and acceptor moieties in sufficiently close proximity to quench the fluorescence. Upon denaturation or melting, and/or hybridization to a target sequence, the donor and acceptors are separated and no quenching occurs, resulting in a fluorescent reaction mixture.

Figure 18:
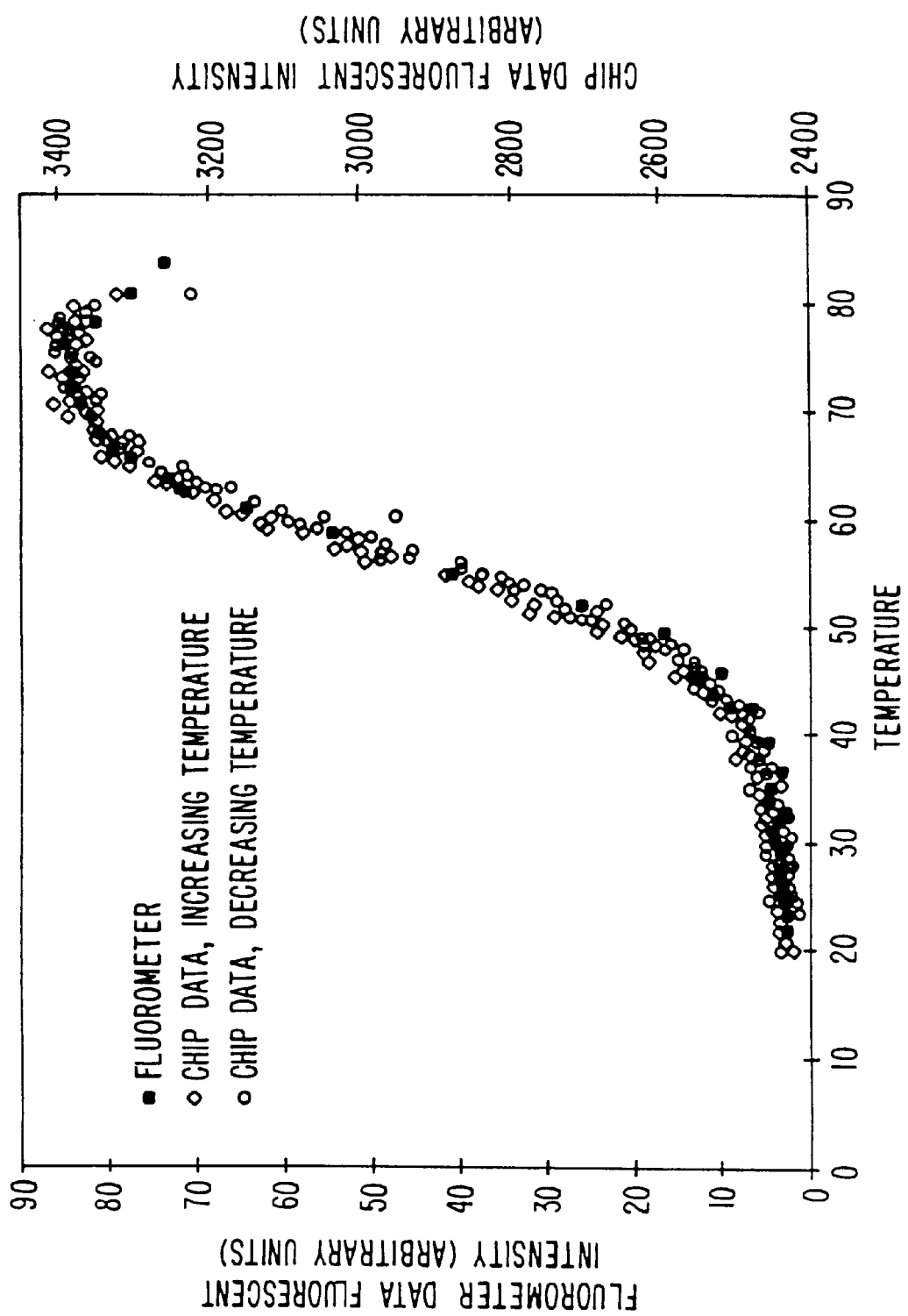
FIG. 18 is a plot of temperatures within a microscale channel, as determined from the measured conductivity of the solution within that channel, which temperatures increase to greater than 100° C. and up to approximately 150° C.

In the experiment performed, a fluid containing a molecular beacon (OswelDNA Service, Southampton, UK) in a 1×
PCR buffer was placed in a microfluidic channel, which included a central portion of narrowed cross-sectional dimension. Heating was controlled by applying current through the channel, and the temperature was determined from the conductivity of the solution. The fluorescence of the solution in the narrow portion of the channel was measured over time, as the current/temperature was first increased from 20° C. to about 95° C., and then decreased back to 20° C. A control run was also performed in a standard fluorometer cuvette, with a water bath providing temperature control, and a thermocouple monitoring the temperature. A plot of the fluorescence is shown in FIG. 18 (diamond-increasing temperature in microscale channel, open circle-decreasing temperature in microscale channel, square-control). As can be seen from the plot in FIG. 18, thermal control of nucleic acid melting by electrical means tracks nearly identically with conventional heating techniques.

While the foregoing invention has been described in some detail for purposes of clarity and understanding, it will be clear to one skilled in the art from a reading of this disclosure that various changes in form and detail can be made without departing from the true scope of the invention. For example, all the techniques described above may be used in various combinations. All publications and patent documents cited in this application are incorporated herein by reference in their entirety for all purposes to the same extent as if each individual publication or patent document were so individually denoted.

What is claimed is:

1. A method of elevating temperature in at least a portion of a fluid-filled channel disposed in a substrate, to a selected elevated temperature, comprising:

applying a selectable current through a fluid in the at least a portion of the fluid-filled channel, the portion of the fluid-filled channel having a electrical resistance;

controlling at least one of the selectable current or the electrical resistance to elevate the temperature in the portion of the channel to the selected elevated temperature.

2. The method of claim 1, further comprising transporting a material through at least the portion of the channel to elevate the temperature of the material to the selected elevated temperature.

3. The method of claim 1, wherein the portion of the channel is at least a first portion and the selected elevated temperature is a first selected elevated temperature, and further comprising maintaining at least a second portion of the channel at a second temperature lower than the first selected elevated temperature.

4. The method of claim 3, further comprising providing the first portion of the channel with a narrowed cross-sectional area relative to the second portion of the channel; and wherein the controlling step comprises applying a constant current through a fluid in the first and second portions of the channel.

5. The method of claim 3, comprising repeatedly transporting a material between the at least first portion of the channel and the at least second portion of the channel to cycle a temperature of the material between the first selected elevated temperature and the second temperature.

6. The method of claim 5, wherein the material comprises reagents for performing a nucleic acid amplification reaction.

7. The method of claim 6, wherein the nucleic acid amplification reaction is selected from the group consisting of a polymerase chain reaction and a ligase chain reaction.

8. The method of claim 2, wherein the transporting of the material comprises electrokinetically transporting the material through the at least first portion.

9. The method of claim 8, wherein the selectable current is a first selectable current, and wherein the step of electrokinetically transporting the material comprises applying a second selectable current through the channel to electrokinetically transport a material along the first channel.

10. The method of claim 9, wherein the first selectable current comprises an alternating current and the second selectable current comprises a direct current.

11. The method of claim 8, wherein electrokinetically transporting the material through the channel comprises electroosmotically transporting the material through the channel.

12. The method of claim 8, wherein electrokinetically transporting the material through the channel comprises electrophoretically transporting the material through the channel.

13. The method of claim 1, wherein the fluid-filled channel is disposed in a substrate, and further comprising the step of maintaining a global temperature of the substrate at a selected level above or below ambient temperature.

14. The method of claim 1, wherein the channel is a first channel, and the applying step comprises:

providing at least a second channel intersecting the first channel at the portion of the first channel; and applying the first selectable current through the second channel and the portion of the first channel.

15. The method of claim 1, wherein the controlling step further comprises sensing a temperature in the portion of the channel, and increasing or decreasing the selectable current based upon the temperature sensed.

16. The method of claim 15, wherein the sensing step comprises determining a relative electrical resistance through the fluid in the portion of the channel, the relative electrical resistance being indicative of the temperature of the fluid in at least the portion of the channel.

17. A method of heating fluid in a microfluidic system, said method comprising steps of;

providing a channel having a first end, a second end, and a region defined therebetween, said channel being disposed in a substrate;

providing fluid in said region of said channel;

applying an electric current through said fluid to heat said fluid at said region;

wherein said electric current selectively heats said fluid in said region of said channel while preventing substantial heating of said fluid outside said region.

18. The method of claim 17, wherein said channel is an annular region.

19. The method of claim 17, wherein said current is applied using a voltage bias applied directly to said fluid.

20. The method of claim 19, wherein said voltage bias is applied directly to said fluid using a pair of electrodes.

21. The method of claim 17, wherein said region has a smaller cross-section relative to a cross-section of said channel at said first end.

22. The method of claim 17, wherein said region has a smaller cross-section relative to a cross-section of said channel at said second end.

23. The method of claim 17, wherein said current is DC, AC, or arbitrary.

24. The method of claim 17, wherein said fluid contains materials selected from the group consisting of samples, analytes, buffers and reagents.

25. The method of claim 17, wherein said channel comprises a cross-section ranging from about 0.1 $\mu$m to about 500 $\mu$m.

26. The method of claim 17, wherein said region is disposed in said substrate adjacent to a second fluid-filled channel disposed in said substrate, but wherein said region is not in direct fluid communication with said second channel.

27. The method of claim 17, further comprising a step of moving said fluid in said channel, said step of moving comprising the steps of applying a voltage bias to said fluid to move said fluid between said first end and said second end.

28. The method of claim 17, wherein said voltage bias is provided by DC.

29. The method of claim 17, wherein said applying step occurs successively to heat and cool said fluid in said region; wherein said applying step selectively heats and cools said fluid in said region of said channel while preventing substantial heating of said fluid outside said region.

30. The method of claim 29, wherein said fluid comprises a nucleic acid material.

31. The method of claim 29, wherein said steps occur in a nucleic acid amplification process.

32. The method of claim 31, wherein the nucleic acid amplification process is selected from the group consisting of PCR and LCR.

33. A method of controlling temperature of fluid in a channel defined in a substrate of a microfluidic system, said method comprising steps of:

applying an electrical energy source to begin heating said fluid in said channel; and adjusting a first parameter applied from said electrical energy source to said fluid to provide a relatively constant second parameter in said fluid, wherein said first parameter is current, voltage, power or a combination thereof, and the second parameter is resistance and conductivity; and wherein said fluid is heated without substantially increasing a temperature of said substrate.

34. The method of claim 33, wherein said first parameter is voltage.

35. The method of claim 33, wherein said first parameter is electric current.

36. The method of claim 33, wherein said second parameter is conductivity.

37. The method of claim 33, wherein said applying step occurs successively to heat and cool said fluid in said channel.

38. The method of claim 33, wherein said fluid is heated in a portion of said channel.

* * * * *

UNITED STATES PATENT AND TRADEMARK OFFICE
CERTIFICATE OF CORRECTION

PATENT NO. : 5,965,410
DATED : October 12, 1999
INVENTOR(S) : Calvin Y.H. Chow, Anne R. Kopf-Sill, J. Wallace Parce It is certified that error appears in the above-identified patent and that said Letters Patent is hereby corrected as shown below:

Col. 36, line 21, please delete "17" and insert --19--.

Signed and Sealed this

Twenty-fifth Day of April, 2000

*Attest:*

Q. TODD DICKINSON

*Attesting Officer*     *Director of Patents and Trademarks*